US012402916B2

(12) United States Patent
Janna et al.

(10) Patent No.: US 12,402,916 B2
(45) Date of Patent: Sep. 2, 2025

(54) CONNECTION MECHANISMS FOR COUPLING PRINTED CIRCUIT BOARD MODULES TO A RING IN AN AUTOMATED AND/OR MOTORIZED SPATIAL FRAME

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Sied W. Janna, Memphis, TN (US); Darren J. Wilson, Hull (GB)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(*) Notice: Subject to any disclaimer, the term of this patent is extended or adjusted under 35 U.S.C. 154(b) by 153 days.

(21) Appl. No.: 17/855,254

(22) Filed: Jun. 30, 2022

(65) Prior Publication Data
US 2023/0008535 A1 Jan. 12, 2023

Related U.S. Application Data

(60) Provisional application No. 63/219,211, filed on Jul. 7, 2021.

(51) Int. Cl.
*A61B 17/66* (2006.01)
*A61B 17/00* (2006.01)
(Continued)

(52) U.S. Cl.
CPC ............ *A61B 17/66* (2013.01); *A61B 17/645* (2013.01); *H05K 1/148* (2013.01); *H05K 5/0217* (2013.01);
(Continued)

(58) Field of Classification Search
CPC ......... A61B 17/62; A61B 17/64; A61B 17/45; A61B 17/66; A61B 2017/00398
See application file for complete search history.

(56) References Cited

U.S. PATENT DOCUMENTS

2002/0010465 A1* 1/2002 Koo ................... A61B 17/62
606/57
2008/0269741 A1* 10/2008 Karidis ............... A61B 17/62
606/56
(Continued)

FOREIGN PATENT DOCUMENTS

WO WO-2021069078 A1 * 4/2021 ............. A61B 17/62

*Primary Examiner* — Eduardo C Robert
*Assistant Examiner* — Holly Joanna Lane
(74) *Attorney, Agent, or Firm* — KDW Firm PLLC

(57) ABSTRACT

An automated and/or motorized spatial frame including a control unit and a plurality of motorized struts is disclosed. The control unit being configured as a controller for exchanging data with an external computing system, exchanging data with the plurality of motorized struts, and delivering power to the motorized struts. Thus arranged, the control unit may be configured as a fully integrated power supply and controller for powering and controlling the motorized struts. In some embodiments, the control unit includes a plurality of PCB modules, each positioned within the spaces or pockets formed between adjacent tabs on a ring of the frame. The PCB modules being detachably coupled to the ring. In some embodiments, the PCB modules may be detachably coupled to the ring via interconnecting male and female connectors. Alternatively, the PCB modules may be detachably coupled to the ring via a plurality of brackets.

18 Claims, 17 Drawing Sheets

(51) Int. Cl.
  *A61B 17/64* (2006.01)
  *H05K 1/14* (2006.01)
  *H05K 5/02* (2006.01)
  *H01R 12/75* (2011.01)
(52) U.S. Cl.
  CPC .... *A61B 2017/00398* (2013.01); *H01R 12/75* (2013.01); *H05K 2201/09018* (2013.01); *H05K 2201/09118* (2013.01); *H05K 2201/10325* (2013.01); *H05K 2201/10424* (2013.01); *H05K 2201/2018* (2013.01)

(56) References Cited

U.S. PATENT DOCUMENTS

| | | | | |
|---|---|---|---|---|
| 2012/0330312 | A1* | 12/2012 | Burgherr | A61B 17/66 606/54 |
| 2015/0088135 | A1* | 3/2015 | Singh | A61B 17/66 606/59 |
| 2015/0238228 | A1* | 8/2015 | Langenfeld | A61B 17/66 606/105 |
| 2017/0071632 | A1* | 3/2017 | Vikinsky | A61B 17/62 |
| 2019/0125456 | A1* | 5/2019 | Shelton, IV | A61B 17/072 |
| 2019/0231259 | A1* | 8/2019 | Cohen | G16H 40/63 |

* cited by examiner

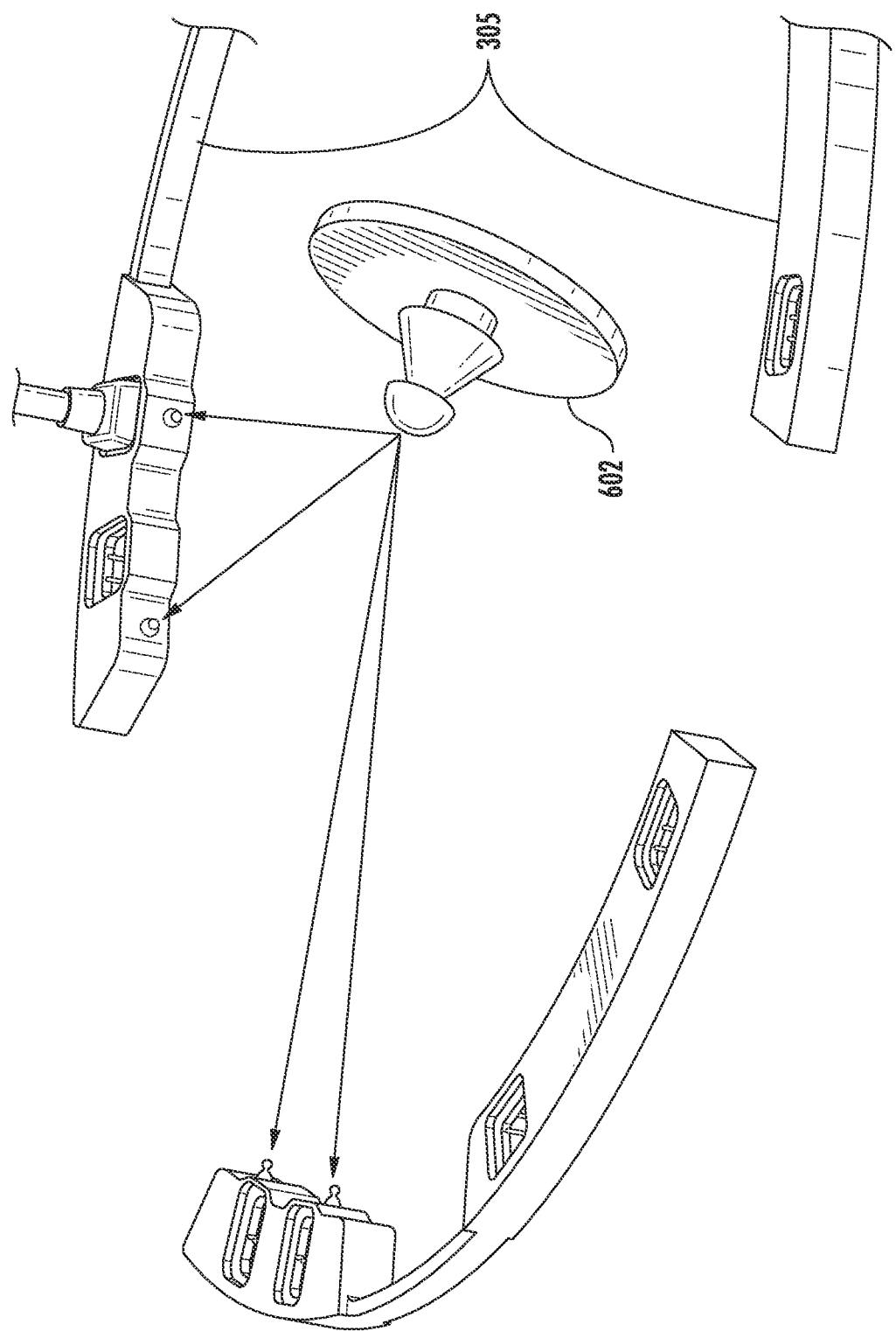

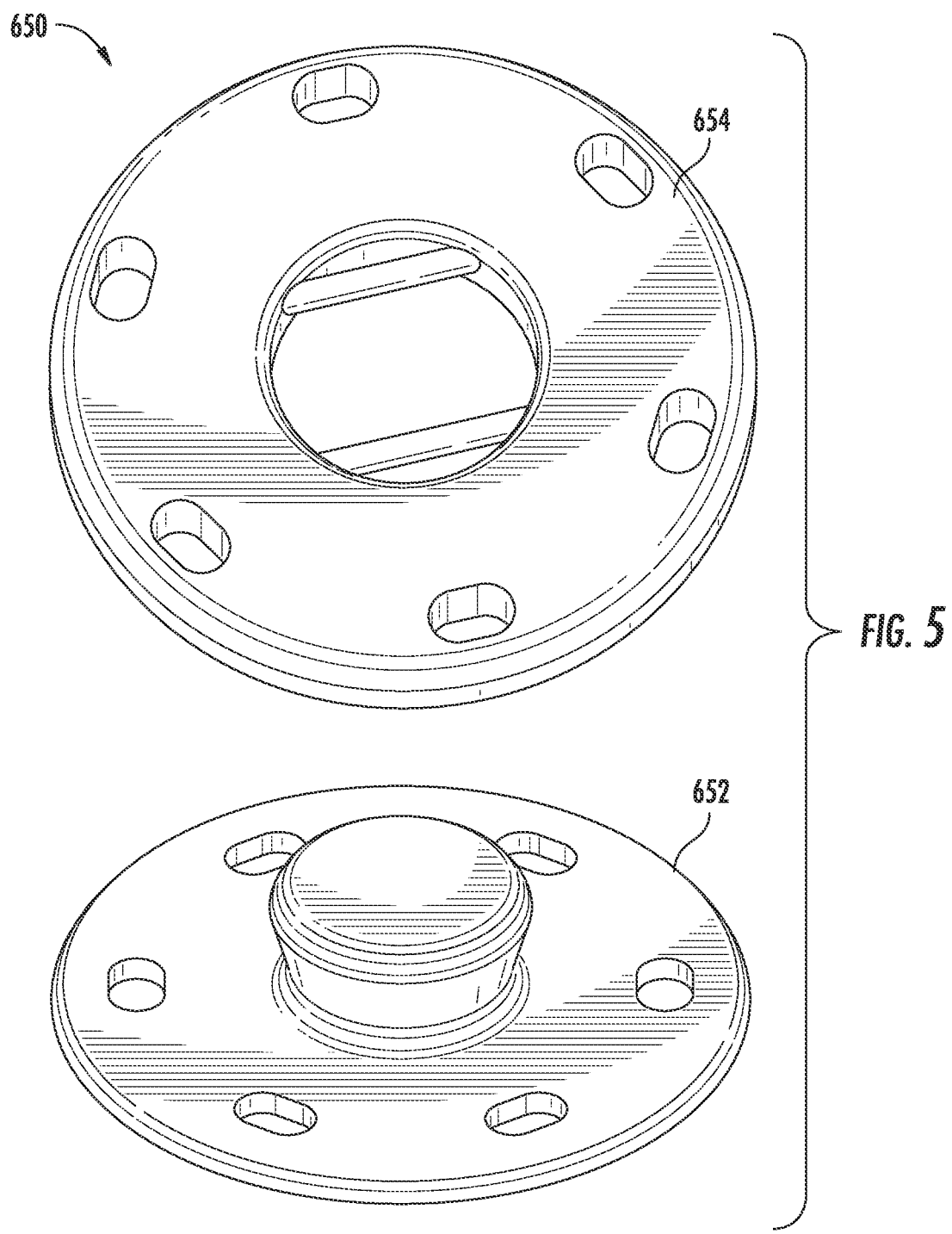

CONNECTION MECHANISMS FOR COUPLING PRINTED CIRCUIT BOARD MODULES TO A RING IN AN AUTOMATED AND/OR MOTORIZED SPATIAL FRAME

CROSS-REFERENCE TO RELATED APPLICATIONS

This is a non-provisional of, and claims the benefit of the filing date of, pending U.S. provisional patent application No. 63/219,211, filed Jul. 7, 2021, entitled "Connection Mechanism for Coupling Printed Circuit Board Modules to a Ring in an Automated Spatial Frame" the entirety of which application is incorporated by reference herein.

FIELD OF THE DISCLOSURE

The present disclosure relates generally to orthopedic devices, systems, and methods for facilitating fracture alignment such as the treatment of musculoskeletal conditions with a spatial frame, and particularly to an automated and/or motorized spatial frame including integrated electronic components and motorized linear actuation devices or struts. The integrated electronic components including a control unit comprising one or more print circuit board (PCB) modules, each positioned within the spaces or pockets formed between adjacent tabs on a ring of the spatial frame. The PCB modules being detachably coupled to the ring using non-threaded connectors such as, for example, interconnecting male and female connectors, brackets, etc.

BACKGROUND OF THE DISCLOSURE

People suffer bone fractures each year. In many instances, a person that suffers a bone fracture is required to use a bone alignment device such as, for example, an external fixation system, a spatial frame, a hexapod, etc. (terms used interchangeably herein without the intent to limit or distinguish) to align two or more bones, bone fragments, bone pieces, etc. (terms used interchangeably herein without the intent to limit or distinguish). Generally speaking, spatial frames allow for polyaxial movement of the coupled bones and are typically used to keep fractured bones stabilized and in alignment during the treatment period.

Generally speaking, the spatial frame may include first and second rings, platforms, frames, bases, etc. (terms used interchangeably herein without the intent to limit or distinguish) intercoupled by a plurality of struts. In use, the struts have adjustable lengths that may be manually adjusted regularly (e.g., daily) in accordance with a prescription or treatment plan (terms used interchangeably herein without the intent to limit or distinguish). As the lengths of the struts are adjusted, the platforms may be brought closer together or moved farther apart. The treatment plan specifies strut length adjustments to be made to each of the struts over time to ensure successful bone alignment. One known example of a spatial frame is the TAYLOR SPATIAL FRAME® manufactured and sold by Smith Nephew, Inc.

The TAYLOR SPATIAL FRAME® is based on the general concept of a Stewart platform. Smith & Nephew, Inc. is the owner of U.S. Pat. Nos. 5,702,389; 5,728,095; 5,891,143; RE40,914, 5,971,984; 6,030,386; and 6,129,727; and U.S. Published patents application Nos. 20030191466; 2004/0073211; 2005/0215997; and 2016/0092651 that disclose many concepts of and improvements to the Stewart platform based spatial frame, including methods of use, systems, and devices that enhance use of the spatial frame. The disclosures of these Smith & Nephew, Inc. patents and applications are hereby incorporated by reference in their entirety herein.

During use, patient's bones are normally adjusted (e.g., lengthened, shortened, etc.) manually, for example, by hand or a wrench at a rate of approximately 1 mm/day, which is then proceeded by a consolidation phase before the spatial frame is removed.

It is theoretically known in the prior art to automate and/or motorize adjustment of a spatial frame by motorizing or otherwise automating strut adjustments. For example, one known motorized strut is the Robotic Hexapod System manufactured by Orthospin Ltd. The Robotic Hexapod System however suffers from a number of disadvantages including being very bulky and having trailing cables, which are used to couple the struts to a centralized controller positioned on top of one of the platforms.

However, currently commercially available spatial frames are dependent on manual adjustment of each strut. As a result of the requirement for manual adjustments, generally speaking, successful treatment requires patient compliance (e.g., daily manual adjustments to each of the struts) to avoid human error. In routine clinical practice, the treatment plan may require multiple daily adjustments to be made to each of the plurality of struts. For example, a patient may be required to manually adjust one or more of the struts, typically two or more times each day, and often over long periods of time with support from either a family member, a clinician, or both. As such, compliance with the treatment plan may be burdensome, painful, and prone to errors, which may rise as the numbers of manual daily adjustments increase.

As a result, the number of adjustments dictated by the treatment plan may be limited. For example, generally speaking, treatment plans often limit the required number of daily adjustments to each of the plurality of struts to four per day. During a normal treatment plan, this may equate to approximately 720 adjustments (e.g., turns) over a one-month treatment span (e.g., 6 struts×4 adjustments per day×30 days). During an extended treatment plan for more severe applications, this may equate to approximately 2,160 adjustments (e.g., turns) over a three-month treatment span (e.g., 6 struts×4 adjustments per day×90 days).

In addition, during the treatment period, the patient may require numerous clinical visits to confirm proper strut adjustments to ensure compliance and avoid incorrect adjustment, which has historically been the leading cause of treatment failure.

Motorized and/or automated spatial frames could provide numerous advantages over manually adjustable struts. In use, electric motors, motor-drive units, and a control unit (e.g., a central control unit) could function to supersede the manual actuation of the strut adjustments. For example, an automated and/or motorized system could eliminate the need for patient compliance and decrease the frequency of post-operative visits for patient supervision given that the spatial frame only has to be activated at the start of the distraction phase and terminated at the end of the distraction phase without any patient intervention. As a result, the burden of manual adjustment can be overcome by automating and/or motorizing the struts, which in turn, enables a more independent lifestyle during treatment.

In addition, as a programmable multi-purpose device, automated and/or motorized spatial frames allow the implementation of more diverse treatment schedules. For example, automatic distraction could enable a higher distraction frequency and result in smaller excursions per activation. Smaller excursions or adjustments have the potential to result in less damage to the distracted tissues, improving bone regeneration and adaptation of the surrounding soft tissues. That is, spatial frames equipped with motorized struts offer the potential to increase the number of daily distraction adjustments by enabling finer (e.g., smaller) adjustments at a controllable rate and frequency of distraction that encourages better quality bone formation. Making finer (e.g., smaller) adjustments during limb lengthening can have significant advantages in terms of reduced soft tissue damage, less pain, and opioid usage and accelerated bone healing. One study has found that the bone fixation index was only 5-6 days/cm when using motorized and/or automated distraction compared to 22-24 days/cm by manual adjustment.

In some embodiments, for example, a motorized strut could be programmed to perform anywhere from one adjustment per day to continuous adjustments. In some embodiments, finer adjustments can increase the number of adjustments over a one-month period from approximately 720 adjustments to approximately 3,600 adjustments (e.g., 6 struts×20 adjustments per day×30 days). In another embodiment, finer adjustments can increase the number of adjustments over a one-month period to approximately 259,200 adjustments (e.g., 6 struts×1440 adjustments per day×30 days). Over an extended three-month treatment period, this could increase the number of adjustments from approximately 2,160 adjustments to approximately 10,800 adjustments (e.g., 6 struts×20 adjustments per day×90 days). In another embodiment, finer adjustments can increase the number of adjustments over a three-month period to approximately 777,600 adjustments (e.g., 6 struts×1440 adjustments per day×90 days).

However, automated and/or motorized spatial frames face a number of challenges that need to be overcome. For example, in order for an automated and/or motorized spatial frame to be practical, the automated and/or motorized spatial frame needs to provide (a) sufficient power to the individual struts in order for them to carry out the required adjustments on a daily basis over the treatment period and (b) needed data connections to the struts, while reducing the overall bulkiness (e.g., size and weight) of the spatial frame and motorized struts so that the spatial frame can be effectively worn by the patient during the treatment period.

As illustrated in one embodiment as provided for in "Bone mounted hexapod robot for outpatient distraction osteogenesis." Robert Wendlandt, F. Wackenhut, K. Seide, J. Müller 4th European Conference of the International Federation for Medical and Biological Engineering 2008, IFMBE Proceedings 22, pp. 1679-1682; and U.S. Pat. No. 9,949,758; automated and/or motorized spatial frame devices in the prior art are fundamentally modified devices that fail to fit within space parameters of typically marketed spatial frames and/or require additional or overly complex mechanisms for implementation.

It would be beneficial if the automated and/or motorized spatial frame and/or the components thereof are substantially similar in size and configuration to existing spatial frames and/or the components thereof. In addition, a control module or unit and battery should be designed to not interfere with spatial frame assembly or operation in order to maintain its prescription freedom. Moreover, it would be beneficial for the automated and/or motorized spatial frame to be provided without any external electronic components such as, for example, batteries, snagging wires/exposed cabling. Otherwise, for example, wires running between the struts and electrical connectors would need to be designed to withstand environmental conditions. In addition, external wiring would need to run within or around the platforms, which could lead to ripping or tearing by the patient during use.

Thus, it would be beneficial to provide an automated and/or motorized spatial frame that includes the necessary controlling electronics that overcome the challenges of the prior art devices. It is with respect to these and other considerations that the present disclosure may be useful.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure illustrates and describes various embodiments of an automated and/or motorized spatial frame. In some embodiments, the automated and/or motorized spatial frame may include a plurality of motorized struts. In addition, the automated and/or motorized spatial frame utilizes a "Smart Ring" including, for example, one or more print circuit board (PCB) modules including a control unit and power supply arranged and configured to provide localized intelligence to supply data and/or power to each of the plurality of motorized struts.

That is, in some embodiments, the present disclosure provides a spatial frame and associated system architectural for an improved motorized, auto-adjusting system. In some embodiments, the spatial frame includes first and second platforms, a plurality of adjustable length, motorized struts coupled to the first and second platforms, and a control unit for controlling the movement of the motorized struts.

In some embodiments, the control unit is arranged and configured to exchange (e.g., transmit and/or receive) data with the plurality of motorized struts. For example, in some embodiments, the control unit is arranged and configured to transmit instructions to the plurality of struts. The instructions including, for example, length adjustment instructions, timing instructions, etc. for each of the plurality of struts.

In some embodiments, additionally and/or alternatively, the control unit is arranged and configured to provide power to each of the plurality of struts. That is, in some embodiments, the control unit may include a power supply so that when the control unit is coupled to the motorized struts, the control unit supplies power to each of the plurality of struts.

In some embodiments, the control unit includes three separate and independent ring-shaped PCB modules. In use, each of the PCB modules is arranged and configured to be coupled to the platform of the spatial frame within the existing spaces or pockets formed between the laterally extending tabs formed on the platforms.

The PCB modules may be coupled to the spatial frame (e.g., platform). In some embodiments, the PCB modules may be detachably coupled to the platform. In some embodiments, the PCB modules are coupled to the platform using one or more quick-coupling mechanical fasteners (e.g., non-threadable connectors).

In some embodiments, the PCB modules are designed to fit within the spaces or pockets between existing tabs formed on the platforms. The detachable PCB modules can be coupled to the platforms using non-threaded connectors such as, for example, interconnecting male and female connectors. In some embodiments, the female connector may be integrated into the platform. For example, in some embodiments, the female connector includes external threads for threadably engaging an internally threaded hole formed in a sidewall of the platforms.

In some embodiments, the male connector is integrated (e.g., moulded) with the individual PCBs modules. In use, the male connector is inserted into (e.g., non-threadably coupled) the female connector thereby coupling the PCB modules to the platforms.

Alternatively, the PCB modules may be coupled to the platform using other suitable non-threaded connectors such as, for example, buttons, toggles, studs, islet and cap, poppers, eyelets, buckles, Velcro, magnetic strip or tape, and adhesive tape.

Alternatively, in other embodiments, the PCB modules may be coupled to the platforms using a plurality of clips. In some embodiments, the clip includes a bracket and a shoulder bolt and nut assembly. The bracket is arranged and configured to surround the PCB module and platform to couple the PCB modules to the platform. In use, the clips can be positioned about the PCB modules and platform as needed. Once positioned, the shoulder bolt may be passed through the bracket and through the existing shoulder bolts openings currently provided in the platform.

In one preferred embodiment, a motorized spatial frame is disclosed. The motorized spatial frame including a first platform; a second platform; and a plurality of motorized struts coupled to the first and second platforms, each of the plurality of motorized struts configured to extend and retract in response to one or more electrical signals One of the first and second platforms include a control unit electrically connected to one or more of the plurality of the motorized struts, the control unit configured to provide the one or more electrical signals to the plurality of motorized struts; a power source configured to supply power to the plurality of motorized struts, the control unit and the power source being configured to reside within spaces between tabs formed on the platform; and plurality of non-threaded connector assemblies arranged and configured to detachable couple the control unit and the power source to the platform.

In some embodiments, the plurality of non-threaded connector assemblies include non-threaded interconnecting male and female connectors.

In some embodiments, the female connectors are integrated into the platform and the male connectors are integrated into the PCB modules.

In some embodiments, the female connectors include external threads for threadably engaging an internally threaded hole formed in a sidewall of the platform.

In some embodiments, the male connectors are molded with the individual PCBs modules.

In another preferred embodiment, a motorized spatial frame is disclosed. The motorized spatial frame including a first platform; a second platform; and a plurality of motorized struts coupled to the first and second platforms, each of the plurality of motorized struts configured to extend and retract in response to one or more electrical signals. One of the first and second platforms includes a control unit electrically connected to one or more of the plurality of the motorized struts, the control unit configured to provide the one or more electrical signals to the plurality of motorized struts; a power source configured to supply power to the plurality of motorized struts, the control unit and the power source being configured to reside within spaces between tabs formed on the platform; and a plurality of clips arranged and configured to detachable couple the control unit and the power source to the platform.

In some embodiments, the plurality of clips include a bracket and a shoulder bolt and nut assembly.

In some embodiments, the bracket is arranged and configured to surround the PCB module and platform to couple the PCB modules to the platform.

In some embodiments, the shoulder bolt passes through the bracket and through an existing shoulder bolt opening formed in the platform.

Embodiments of the present disclosure provide numerous advantages. For example, by enabling a non-threaded, detachable connection between the control unit (e.g., PCB modules) and the platforms, semi-continuous actuation without compromising the ability to carry out complex limb deformity corrections with a spatial frame is achieved. The PCB modules can be attached to the frame in a clinic setting negating the need for any sterilization. In addition, a simplified overall design of the automated and/or motorized spatial frame is achieved thereby reducing the risk of an electrical failure during application.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, specific embodiments of the disclosed device will now be described, with reference to the accompanying drawings, in which:

FIG. 3E illustrating the underlying electronics while FIG. 3F omits the underlying electronics for increased clarity;

FIG. 4D illustrates a perspective view of the male connector shown in FIG. 4B being molded within each PCB module;

FIG. 5 illustrates a perspective view of an embodiment of an islet and a cap that could be used to couple the detachable PCB modules to a ring or platform of a spatial frame in accordance with one or more features of the present disclosure;

Figure 1:
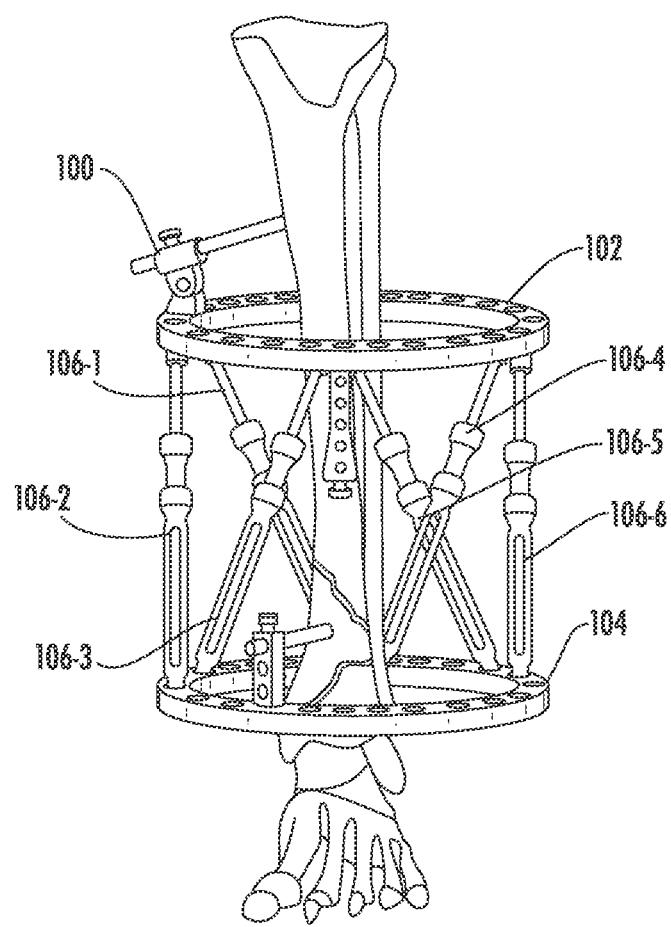
FIG. 1 illustrates an embodiment of a spatial frame.

The drawings are not necessarily to scale. The drawings are merely representations, not intended to portray specific parameters of the disclosure. The drawings are intended to depict various embodiments of the disclosure, and therefore are not to be considered as limiting in scope. In the drawings, like numbering represents like elements.

DETAILED DESCRIPTION

Various features or the like of an automated and/or motorized spatial frame (terms automated and/or motorized used interchangeably herein) will now be described more fully herein with reference to the accompanying drawings, in which one or more features of the spatial frame will be shown and described. It should be appreciated that the various features may be used independently of, or in combination, with each other. It will be appreciated that a spatial frame as disclosed herein may be embodied in many different forms and may selectively include one or more concepts, features, or functions described herein. As such, the spatial frame should not be construed as being limited to the specific embodiments set forth herein. Rather, these embodiments are provided so that this disclosure will convey certain features of the spatial frame to those skilled in the art.

As will be described in greater detail, in use, the spatial frame includes a plurality of motorized external fixation struts, automated struts, or the like (terms used interchangeably herein without the intent to limit or distinguish) coupled to first and second platforms. In use, movement of the motorized struts move the first and second platforms, and hence the first and second bone portions coupled thereto.

As previously disclosed in International Patent Application No. PCT/US20/52276, filed on Sep. 23, 2020, entitled "Automated Spatial Frame and Automated Struts Used Therewith," the entire contents of which application is hereby incorporated in its entirety herein, in some embodiments, the automated and/or motorized spatial frame may include a control unit coupled to one of the platforms of the spatial frame, the control unit may be in the form of or include one or more printed circuit board (PCBs) modules, which may be incorporated into a Smart Ring as will be described in greater detail herein. The PCB modules may be detachably coupled to the platform (e.g., ringed-shaped platform) in a sleek, efficient profile.

For example, as will be described in greater detail herein, the control unit may be provided as three separate mini-rings or PCB modules, although alternate configurations are envisioned including, for example, more or less PCB modules such as one, two, four, or more. Each PCB module is coupled to a ring or platform of the spatial frame. In some embodiments, each of the PCB modules is arranged and configured to be positioned within the existing spaces or pockets between adjacent tabs formed on the ring or platform of the spatial frame. Thus arranged, the controlling electronics may be embedded within the spaces or pockets between the tabs. In use, the PCB modules control the movement of the six motorized struts. For example, if three PCB modules are utilized, each PCB module may be responsible for controlling two motorized struts.

As will be described herein, in use, the control unit (e.g., PCB modules) may be arranged and configured to: (i) deliver power to the motorized struts; (ii) exchange positional data and/or instructions with the motorized struts; (iii) control each of the motors of the motorized struts for which it is responsible; and (iv) store and update current positional data associated with each of the motorized struts. In addition, the control unit (e.g., PCB modules) may be arranged and configured to communicate with an external computing system to, for example, receive spatial frame treatment plans and/or updates.

The control unit (e.g., PCB modules) may communicate with the external computing system via any suitable mechanism now known or hereafter developed. For example, via a wired network or connection, such as a USB connection, via wireless communication or a wireless network. For example, the control unit (e.g., PCB modules) may include a communication transceiver for communicating with the external computing system. In use, the control unit (e.g., PCB modules) and the external computing system are communicatively coupled to exchange data such as, for example, treatment plan information, updates, strut positional data, etc. In use, with the treatment plan downloaded onto the control unit (e.g., PCB modules) and with the control unit (e.g., PCB modules) operatively coupled to the platform and/or motorized struts, the control unit (e.g., PCB modules) can supply power to the struts and convert the treatment plan into instructions to control each of the motorized struts. Thus arranged, the external computing system may connect to the control unit (e.g., PCB modules) to control the plurality of motorized struts. The struts may move individually (e.g., sequentially) or simultaneously according to the treatment plan. In addition, the control unit (e.g., PCB modules) may periodically supply real time actuation data and/or updates to the external computing system thereby conforming compliance with the treatment plan.

In use, the external computing system may be any suitable external computing system now known or hereafter developed including, for example, a desktop computer residing, for example, in a surgeon's office, a laptop, an APP running on a smartphone, a tablet, etc., or combinations thereof. In use, the communication transceiver may be any suitable communication interface now known or hereafter developed including, for example, wired and wireless transceivers. For example, the communication interface may be a wireless communication transceiver for wirelessly communicating with the external computing system.

Thus arranged, the control unit (e.g., PCB modules) may be arranged and configured to exchange data such as, for example, a treatment plan, with the external computing system and to exchange data such as, for example, adjustment instructions, with the plurality of motorized struts. In addition, the control unit (e.g., PCB modules) may be arranged and configured to deliver power to the plurality of motorized struts. Thus arranged, the control unit (e.g., PCB modules) may be arranged and configured to control and/or power the plurality of motorized struts.

Referring now to the drawings, FIG. 1 illustrates an embodiment of a bone alignment device such as, for example, an external fixation system, a spatial frame, a hexapod, etc. 100 (terms used interchangeably herein without the intent to limit or distinguish). As shown in FIG. 1, the spatial frame 100 may form a hexapod having a circular, metal frame with a first platform 102 and a second platform 104 connected by six adjustable length struts 106 (labeled as struts 106-1 through 106-6 in FIG. 1). Each strut 106 may be independently lengthened or shortened relative to the rest of the frame, thereby allowing for six different axes of movement.

Each strut 106 may include an outer body and an inner body, which may be configured as, or be operatively coupled to, a threaded rod or lead screw (terms used interchangeably without the intent to limit or distinguish). The outer body may be coupled to one of the platforms, such as, the second platform 104 by way of a joint as shown. The inner body may be coupled to the other platform, such as, the first platform 102 by way of a joint as shown. To lengthen or shorten one of struts 106, the outer body and the inner body may be moved or translated relative to one another. For example, in some embodiments, the strut 106 may include an adjustment nut wherein rotation of the adjustment nut moves the inner body (e.g., lead screw) relative to the outer body to adjust an overall length of the strut.

In use, the spatial frame 100 may be used to treat a variety of skeletal fractures of a patient. Typically, the spatial frame 100 is positioned around the patient's bone portions and is used to align two or more bone portions. To do so, a length of each strut 106 may be incrementally adjusted (e.g., shortened or lengthened) in accordance with a treatment plan that specifies adjustments to be made to each strut 106 over time to ensure successful bone alignment. In many instances, the length of each strut 106 should be adjusted daily to comply with the provided treatment plan. Adjusting the length of each strut 106 adjusts the distance between the first and second platforms 102, 104, and hence the first and second bone portions coupled thereto.

In accordance with one of the features of the present disclosure, each strut 106 may include a motor and may be used in a spatial frame such as, for example, spatial frame 100, to move the first and second platforms 102, 104, respectively, to align two or more bones. In use, the spatial frame and/or system architectural may be arranged and configured to automatically adjust the motorized struts according to the prescribed treatment plan (e.g., automatically adjust the plurality of motorized struts without patient intervention-manual adjustments of each of the plurality of struts is not required). Alternatively, the spatial frame and/or system architecture may be arranged and configured to require patient and/or caregiver activation to begin the process of automatically adjusting the motorized struts according to the prescribed treatment plan. For example, the spatial frame may be arranged to intermittently auto-adjust the motorized struts at predetermined times according to the treatment plan. Alternatively, the spatial frame may be arranged to intermittently auto-adjust the motorized struts at select times when convenient and/or selected by the patient. Alternatively, the spatial frame may be arranged and configured to continuously auto-adjust the motorized struts in small discrete increments. In either event, by providing an automated, auto-adjusting spatial frame (e.g., a motorized, auto-adjusting spatial frame), the motorized struts may be adjusted in higher frequency, smaller discrete increments thereby facilitating clinical advantageous as previously discussed.

In some embodiments, the spatial frame in accordance with the present disclosure includes, first and second platforms, a plurality of motorized struts coupled to the first and second platforms, and a control unit arranged and configured to communicate with the motorized struts. In some embodiments, the control unit is arranged and configured to supply power to the motorized struts and to exchange (e.g., receive and/or transmit) data with the motorized struts.

Figure 2:
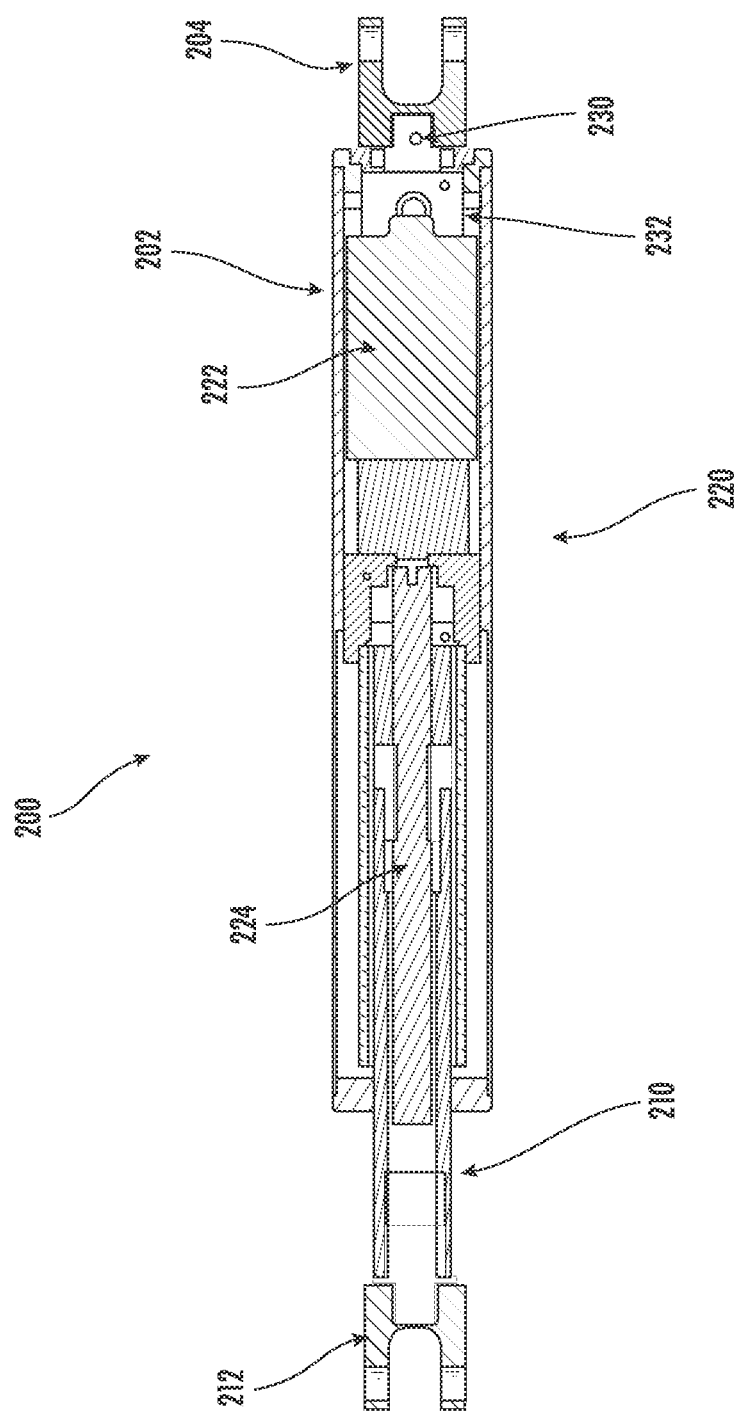
FIG. 2 illustrates a cross-sectional view of an embodiment of a motorized strut that may be used in a spatial frame in accordance with one feature of the present disclosure.

Referring to FIG. 2, an embodiment of a motorized strut 200 is disclosed. In use, the motorized strut 200 may be coupled to first and second platforms in a spatial frame. For example, the motorized strut 200 may be used in place of the manually adjustable struts 106 shown in FIG. 1. As shown in FIG. 2, the motorized strut 200 may include an outer body 202 operatively coupled with a first joint 204 for coupling to a first platform, an inner body 210 operatively coupled with a second joint 212 for coupling to a second platform, and a drive mechanism, actuator, etc. 220 (terms used interchangeably herein without the intent to limit or distinguish). In use, actuation of the drive mechanism 220 moves the inner body 210 relative to the outer body 202 to adjust a length of the motorized strut 200.

The first and second joints 204, 212 may have any suitable configuration now known or hereafter developed such as, for example, shoulder bolts, U-joints, etc. In use, the first and second joints 204, 212 are arranged and configured to couple the motorized struts to the platforms at predefined locations as will be appreciated by one of ordinary skill in the art.

As illustrated, in some embodiments, the drive mechanism 220 may include a motor 222 and a lead screw 224 arranged and configured so that, in use, actuation of the motor 222 rotates the lead screw 224, which moves the inner body 210 relative to the outer body 202 to adjust an overall length of the motorized strut 200. In addition, the drive mechanism 220 may include one or more gears to adjust speed and torque of the motor 222.

In addition, the motorized strut 200 may include any required circuitry. That is, automated or autonomous, motorized spatial frames may incorporate a number of mechanical and electrical components. For example, each motorized strut 200 may include a control circuit that controls the motor speed and direction according to the treatment plan. A motor control circuit may also provide hardware and software protections that prevent any deviation from the treatment plan and alert the patient in the event of a malfunction.

In some embodiments, for example, the motorized strut 200 may include one or more position sensors to, for example, monitor absolute position or length of the strut 200. In addition, and/or alternatively, the motorized strut 200 may include other sensors for monitoring various biomechanical parameters such as, for example, a force sensor 230 for monitoring stresses and forces, across the bone gap and/or the soft tissues (muscle, apposing cartilage or peripheral sensory nerves), an accelerometer for capturing patient ambulation data (steps, distance, speed and cadence), a gyroscope for measuring the degree of alignment between the bone fragments, a sensor motor support 232, etc. In addition, and/or alternatively, the motorized strut 200 may include an encoder such as, for example, a rotary encoder for measuring rotation of the motor 222 for accurate positioning and motion control. In addition, and/or alternatively, the strut 200 may include memory for storing unique identifiers (e.g., addresses) and for storing current position, biomechanical and ambulatory data, etc.

In use, in some embodiments, the motorized struts 200 are arranged and configured to receive power and to exchange data with the control unit (e.g., PCB modules). In some embodiments, the motorized struts 200 may be operatively coupled to the control unit via, for example, a hardwired connection, although it is envisioned that the motorized struts may receive power and/or exchange data with the control unit by any other suitable mechanism now known or hereafter developed including, for example, wireless power and/or data transmission. In any event, as will be described in greater detail, the motorized struts 200 may be arranged and configured to be operatively coupled to the control unit for receiving power, exchanging data, or a combination thereof.

By arranging the motorized struts 200 so that they receive power from the control unit, the motorized struts 200 need not incorporate individual power supplies (e.g., a battery, etc. as such each motorized strut 200 may be battery-less or devoid of any power supply), although it is envisioned that the motorized struts may incorporate a power supply unit (e.g., battery). By providing a battery-less motorized strut, design and manufacture of the motorized struts is simplified thereby minimizing, or at least reducing, strut complexity and thus likelihood that individual struts will fail.

As will be described in greater detail below, the motorized struts 200 include a communications interface for coupling to the control unit. In use, in some embodiments, the communication interface may be used to exchange data with the control unit and/or to receive power from the control unit. The communication interface may be any suitable interface now known or hereafter developed. For example, in some embodiments, as will be described in greater detail below, the struts 200 may be coupled to the PCB modules via one or more pogo pin connector and socket assemblies.

In some embodiments, the motorized struts 200 may be water-proofed to facilitate the patient, for example, taking a shower or bath. For example, bellows may be coupled to the ends of the struts or the individual external housing components of the strut may be sealed with O-rings. Alternatively, it is envisioned that the motorized struts and/or the spatial frame may be covered by, for example, a bag during a shower thus alleviating the necessity for waterproofing each of the motorized struts.

As will be described herein, the spatial frame and corresponding system architectural according to the present disclosure may be used with any suitable motorized strut now known or hereafter developed. In this regard, the present disclosure should not be limited to the details of the motorized strut disclosed and illustrated herein unless specifically claimed. Rather, it should be understood that any suitable motorized strut may be used in connection with the principles of the present disclosure.

As previously mentioned, the spatial frame includes a control unit. In some embodiments, as will be described in greater detail below, the control unit may be in the form of one or more PCB modules positioned between the spaces or pockets formed in the ring or platform 102, 104, the spaces or pockets located between the laterally extending tabs on the existing ring or platform 102, 104. Thus arranged, the ring or platform 102, 104 and the PCB modules may be referred to as a Smart Ring (e.g., as will be described in greater detail herein, the Smart Ring 301 may be interpreted to encompass the platform and the control unit 300 inclusive of the plurality of PCB modules including any necessary power supply units and integrated connectivity). As described herein, in some embodiments, the Smart Ring is designed to control the movements and manage the power requirements of the motorized struts such as, for example, motorized struts 200. That is, for example, the Smart Ring is arranged and configured as centralized controllers to control each of the plurality of struts.

In use, the Smart Ring includes any circuitry necessary to control actuation of the motorized struts. For example, in some embodiments, the Smart Ring includes one or more processors, controllers, or the like for implementing the treatment plan (e.g., controlling/providing data such as, for example, adjustment instructions to each of the motorized struts). In addition, the Smart Ring may include memory for storing information such as, for example, treatment plan information, strut information including unique identifiers or addresses for each of the struts, target strut length for each of the struts, absolute strut length for each of the struts, lengthening direction for each of the struts, rate of distraction for each of the struts, rhythm and/or timing of distraction for each of the struts, total amount of distraction for each of the struts, lengthening schedule, number of motor turns, force exerted, etc. In addition, the Smart Ring may include a real-time clock. Additionally, as will be described in greater detail below, the Smart Ring may include a communication interface for communicating with the motorized struts. In addition, the Smart Ring may include a second communication interface for communicating with an external computing system and, in connection with preferred embodiments where the Smart Ring includes three-separate and distinct PCB modules, a communication interface so that each PCB module can communicate with the other PCB modules.

In some embodiments, the Smart Ring may be arranged and configured to synchronize movements of the struts. For example, the Smart Ring may be arranged and configured to control each strut simultaneously or individually. Alternatively, the Smart Ring may be arranged and configured to control each strut sequentially (e.g., the Smart Ring may be arranged and configured to control (adjust) each of the struts sequentially (e.g., one at a time), or in any combination thereof).

In some embodiments, the motorized struts may be arranged and configured to transmit data to the Smart Ring. For example, the struts may include one or more sensors for transmitting data pertaining to strut position, forces acting upon the strut, motor temperature, motor current, etc. to the Smart Ring.

In addition, in some embodiments, the Smart Ring includes one or more power supply units for supplying power to the internal electronics (e.g., micro-processor, communication transceivers, memory, etc.) and for delivering power to each of the motorized struts to power the motors of the motorized struts to adjust the length of the struts and to power internal circuitry contained within the struts.

Referring to FIGS. 3A-3H, an embodiment of an automated and/or motorized spatial frame 275 is disclosed. As illustrated, the automated and/or motorized spatial frame 275 may include one of the first and second platforms, such as, for example, platforms 102, 104, a plurality of motorized struts 200, and a control unit 300. As illustrated and as previously mentioned, the control unit 300 is arranged and configured to be positioned or housed in the redundant pockets or spaces 109 existing between adjacent ring tabs 108 formed in one or both of the platforms (shown as platform 104). That is, the platform 104 may include a plurality of pockets or spaces 109 positioned between the tabs 108 formed in the platform for housing the control unit 300.

As described herein, the control unit 300 and the platform 104 may be referred to as a "Smart Ring" 301 (e.g., the Smart Ring 301 encompassing the platform 104 and the control unit 300 inclusive of the plurality of PCB modules as will be described herein including any necessary power supplies and integrated connectivity). In use, the Smart Ring 301 may be arranged and configured to substantially match the existing profile of a standard ring or platform while providing or incorporating one or more control units and integrated power supplies arranged and configured to provide localized intelligence to supply data and/or power to each of the plurality of motorized struts 200. In addition, the Smart Ring 301 may incorporate integrated connectivity to enable connection to the motorized struts 200. For example, a wire loom or cable arranged and configured to provide data and/or power to the motorized struts 200 may be provided. In some embodiments, as will be described herein, the wire loom or cable may be arranged and configured with local terminations such as, for example, pogo pin connector and socket assemblies, at each of the six tabs 108 formed on the platform.

Figure 3A:
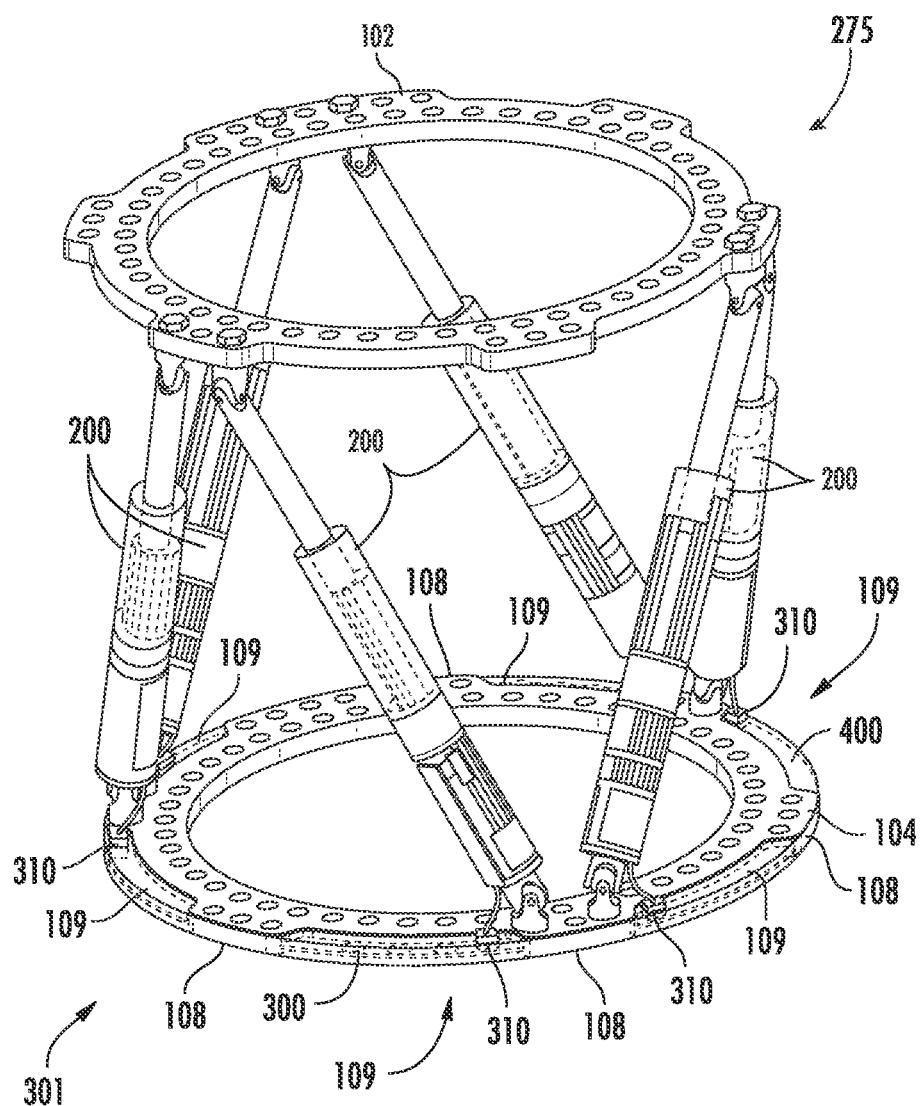
FIG. 3A illustrates a perspective view of an embodiment of an automated and/or motorized spatial frame including a Smart Ring (e.g., an integrated control unit and power supply) in accordance with one or more features of the present disclosure.
Figure 3B:
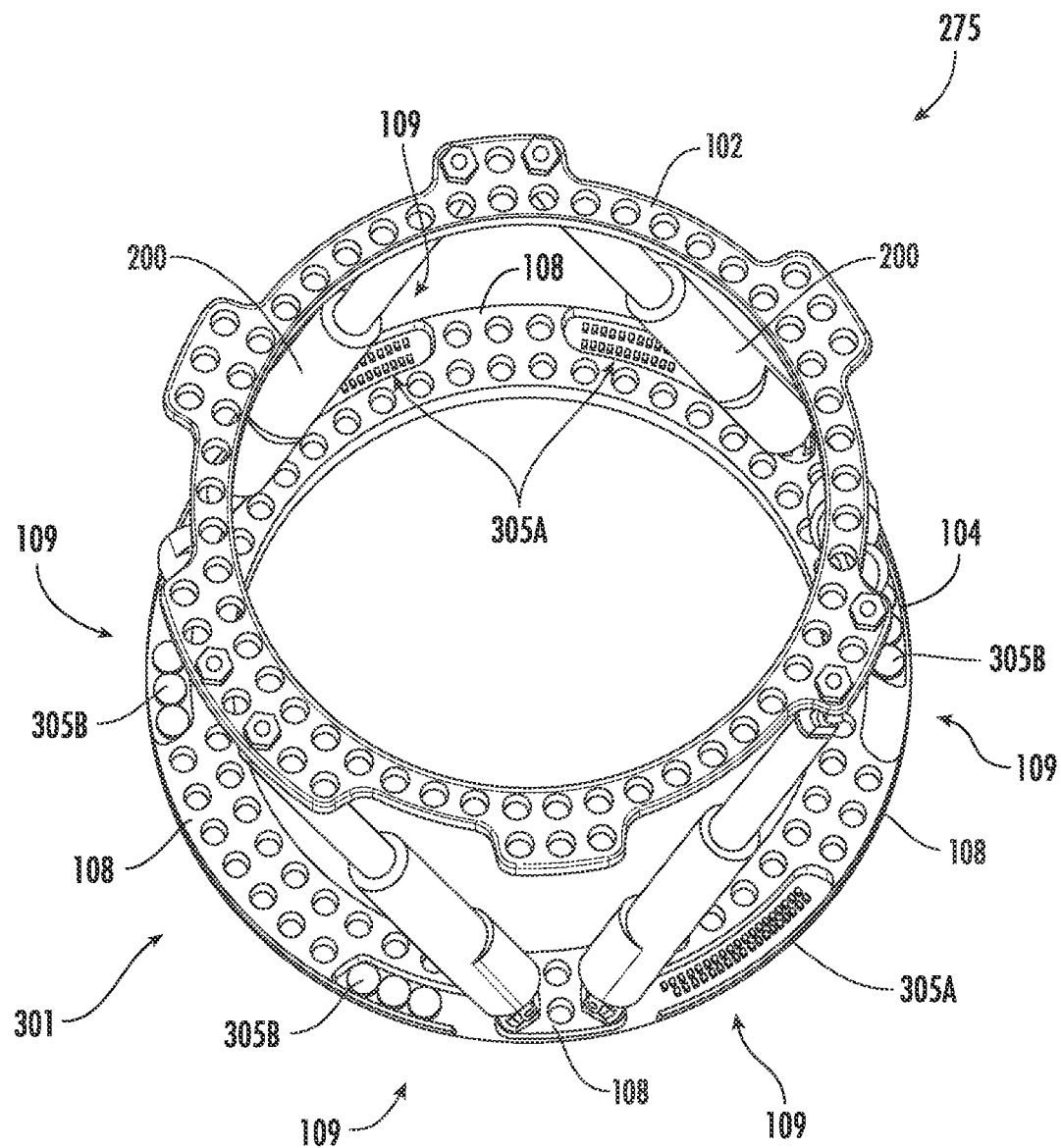
FIG. 3B illustrates a top, perspective view of the spatial frame including the Smart Ring shown in FIG. 3A.
Figure 3C:
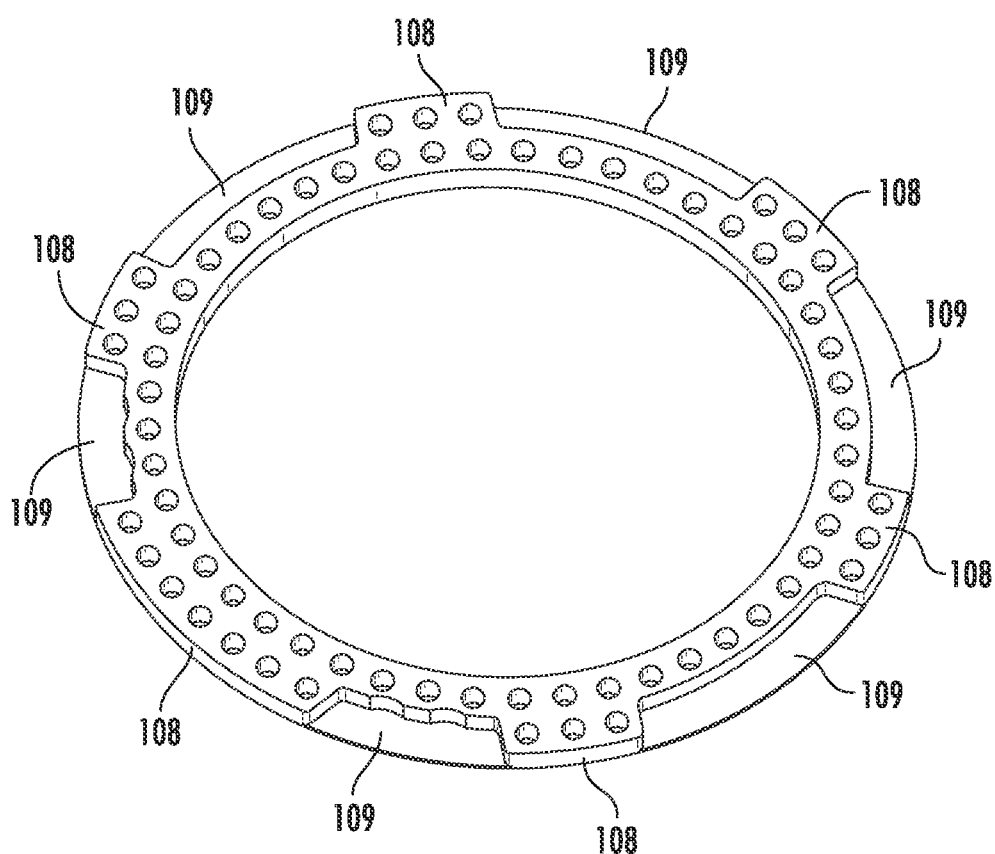
FIG. 3C illustrates a top, perspective view of an embodiment of a platform that may be used in conjunction with the Smart Ring shown in FIG. 3A.
Figure 3D:
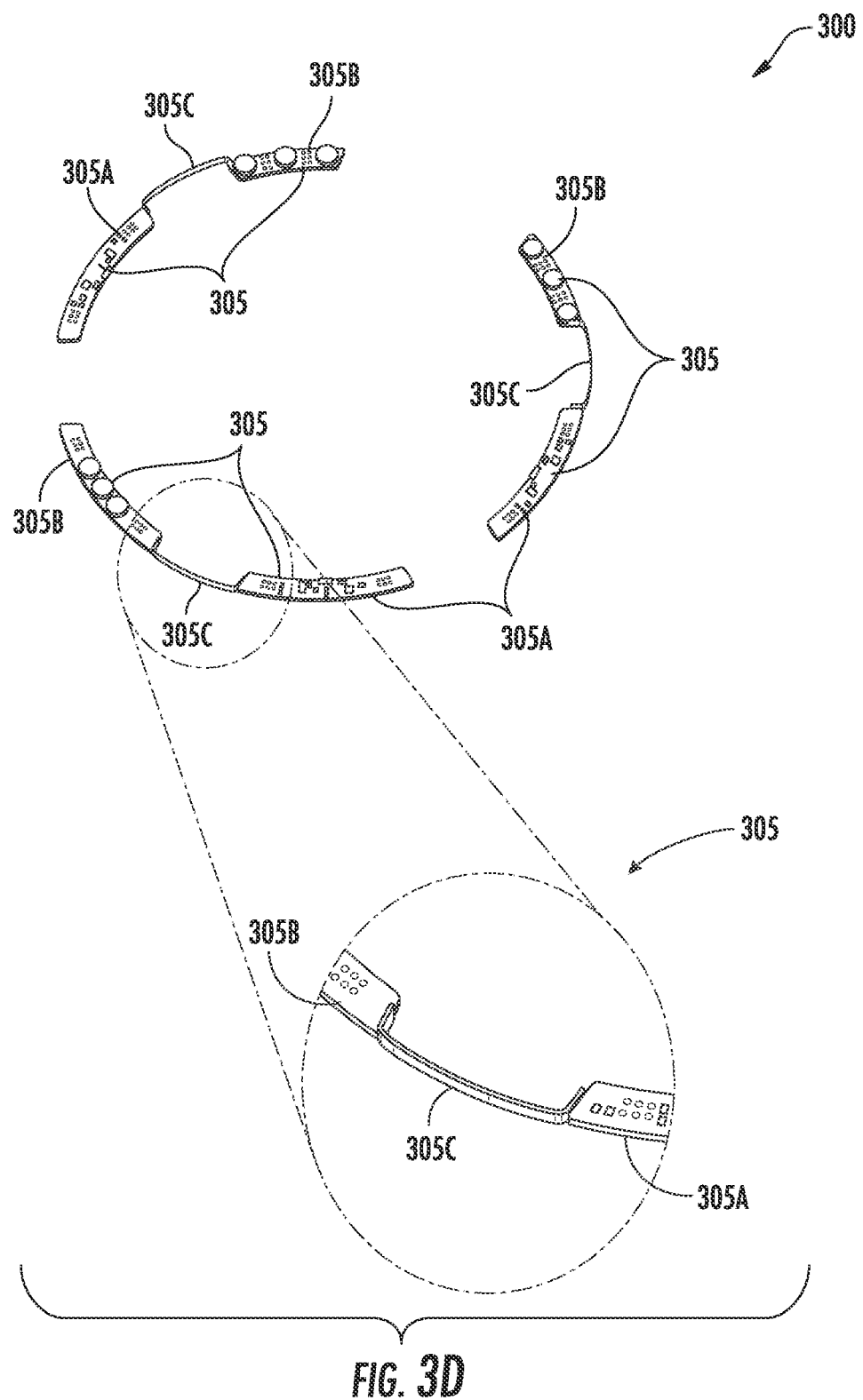
FIG. 3D illustrates a top, perspective view of an embodiment of the control unit that may be used in conjunction with the Smart Ring shown in FIG. 3A, the control unit including independent PCB modules.

Referring to FIG. 3D, in some embodiments, the control unit 300 and thus the Smart Ring 301 may include a plurality of independent PCB modules 305. Each PCB module 305 may include the necessary controls, electronics, and power supply (e.g., batteries such as, for example, three-coin cells) for controlling and powering the motorized strut 200 coupled thereto. For example, as illustrated, the Smart Ring 301 may include three PCB modules 305, the three PCB modules 305 being positioned into the pockets 109 formed in the platform 104. Thus arranged, each PCB module 305 is positioned within one or more of the pockets 109.

In use, in the illustrated embodiment of FIGS. 3A-3H, each PCB module 305 may include the needed circuitry, power, and connectivity to control two (2) motorized struts 200. For example, as illustrated, the Smart Ring 301 may include three PCB modules 305 with each PCB modules 305 including a PCB board 305A and a battery board 305B coupled to each other via a connector 305C. In use, the PCB board 305A may include, for example, the microcontroller and associated electronics. The battery board 305B may include the power supply and associated electronics.

In use, the three PCB modules 305 are positioned within the pockets 109 formed in the platform 104. Each of the PCB boards 305A and the battery boards 305B are arranged and configured to be positioned within one of the pockets 109 formed in the platform 104. For example, each of the PCB boards 305A and the battery boards 305B may be orientated horizontally within its respective pocket 309. In use, each PCB module 305 (e.g., each PCB board 305A and the battery board 305B combo) is responsible for powering and controlling a pair of motorized struts 200. Thus arranged, the Smart Ring 301 may include three independent PCB modules 305 with each PCB module 305 responsible for powering and controlling two motorized struts. Thus arranged, each PCB module 305 may be independently powered and operated as a stand-alone system. In some embodiments, each of the PCB modules 305 may communicated with the other PCB modules 305 wirelessly such as, for example, by Bluetooth Low Energy (BLE) or the like. Alternatively, each of the PCB modules 305 may communicated with the other PCB modules 305 via a wired connection.

In addition, as illustrated, electrical connection between the PCB board 305A and the battery board 305B in each PCB module 305 across the tabs 108 in the platform 104 may be achieved using a flexi/flex-rigid PCB connector 305C positioned in a narrow trench or groove formed in the platform 104. For example, a groove or recess may be provided in an arc in the perimeter of the platform 104 to accommodate the flex rigid PCB connector 305C.

As illustrated, in some embodiments, the battery boards 305B may each include a plurality of coin cell batteries. For example, each battery board 305B may include 3-coin cells, although this is but one configuration and other numbers and types of batteries may be utilized.

In some embodiments, each PCB module 305 may also be arranged and configured with connectors 310 for exchanging data and providing power to the motorized struts 200. In some embodiments, the Smart Ring 301 may include a total of twelve connectors 310, although this is but one configuration. In use, the connectors 310 may be any suitable connector arranged and configured to enable power and data transfer between the motorized struts 200 and the Smart Ring 301 including, for example, jack plugs and sockets, a header connector, etc. In some embodiments, referring to FIGS. 3G and 3H, the connectors 310 may be in the form of a pogo pin connector and socket assembly 500. Thus arranged, connection of the motorized struts 200 with the Smart Ring 301 to supply power and/or data may be via the pogo pin connector and socket assemblies 500.

As illustrated, generally speaking, each pogo pin connector and socket assembly 500 includes a connector component 502 and a socket component 504. As illustrated, the socket component 504 may be formed or positioned within the platform portion of the Smart Ring 301, although the opposite is envisioned. In some embodiments, the pogo pin connector and socket assemblies 500 enable six wired connections between the PCB modules 305 and the motorized struts 200. As illustrated, in some embodiments, the pogo pin connector and socket assemblies 500 may include a key 510 such as for example, interlocking projection and recess, to facilitate installation of the connector component 502 into the socket component 504, a retention feature to ensure a reliable electrical connection is maintained, and a seal 512.

Figure 3E:
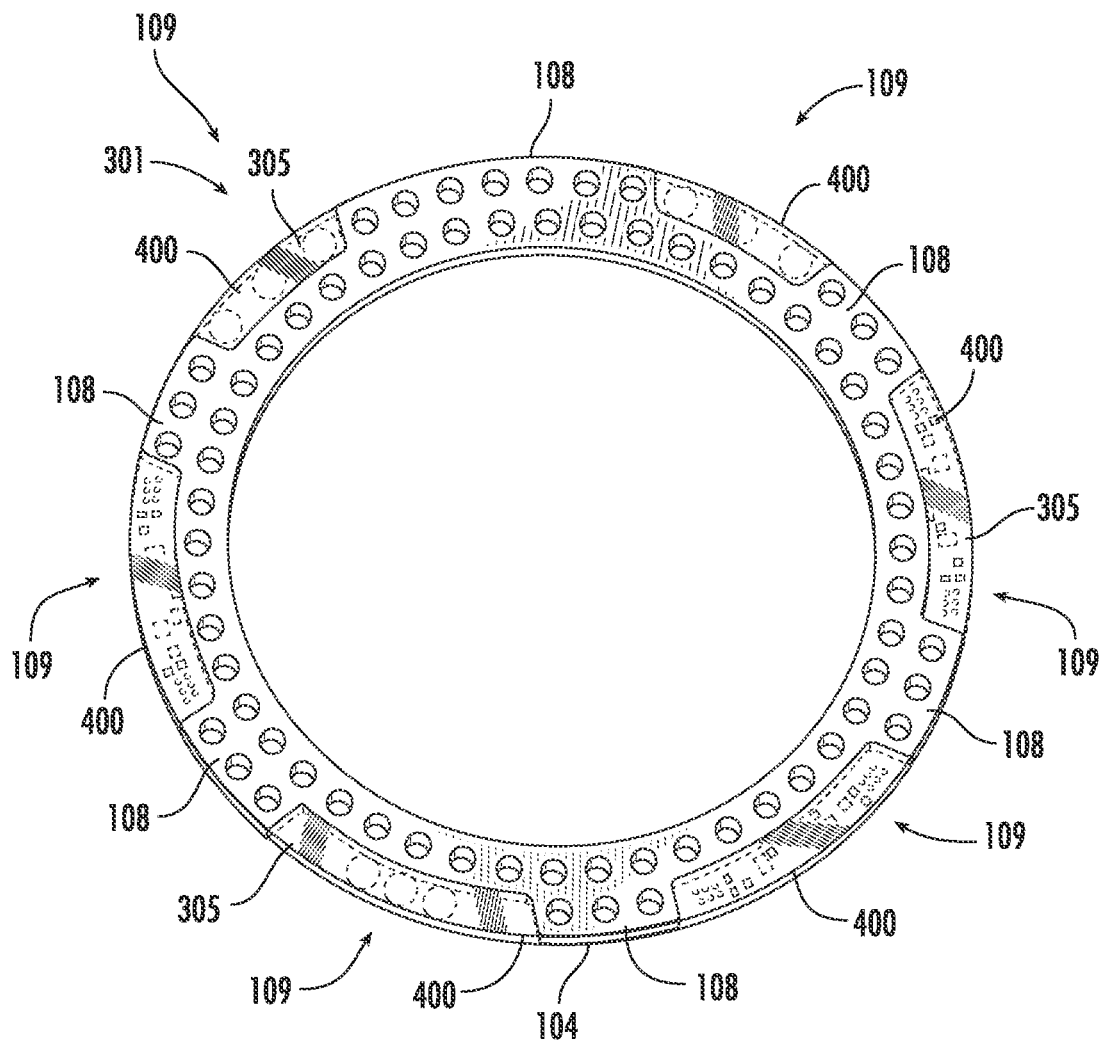
FIGS. 3E and 3F illustrate top, perspective views of the Smart Ring shown in FIG. 3A, the Smart Ring including overmoulding to protect the electronics positioned in the pockets of the platform.
Figure 3F:
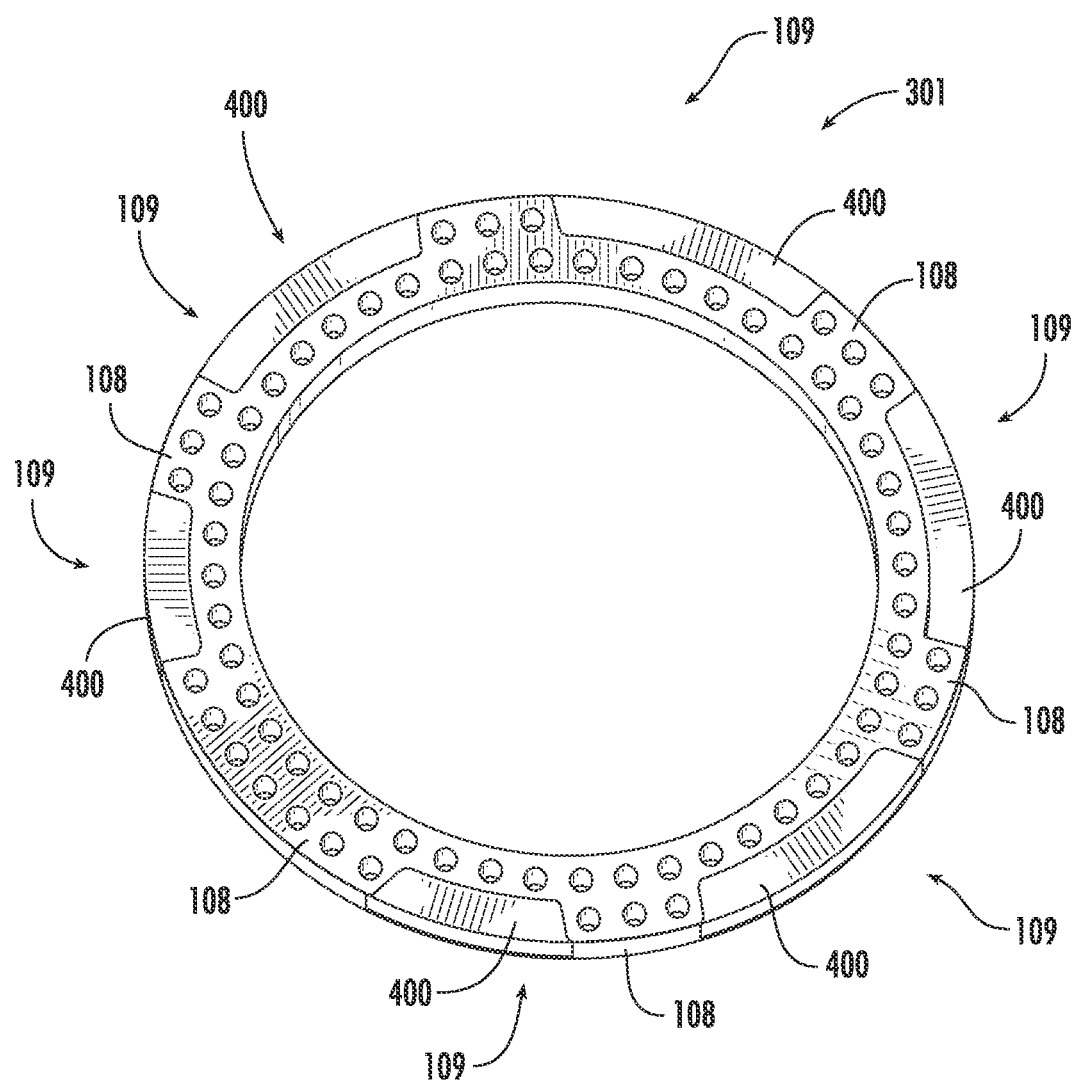
Figure 3G:
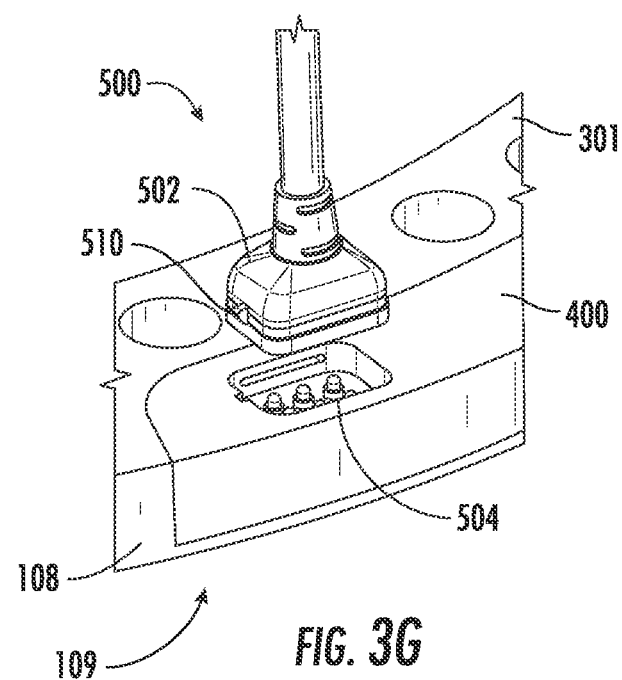
FIG. 3G illustrates an embodiment of a pogo pin connector and socket assembly that may be used in the automated and/or motorized spatial frame of FIG. 3A.
Figure 3H:
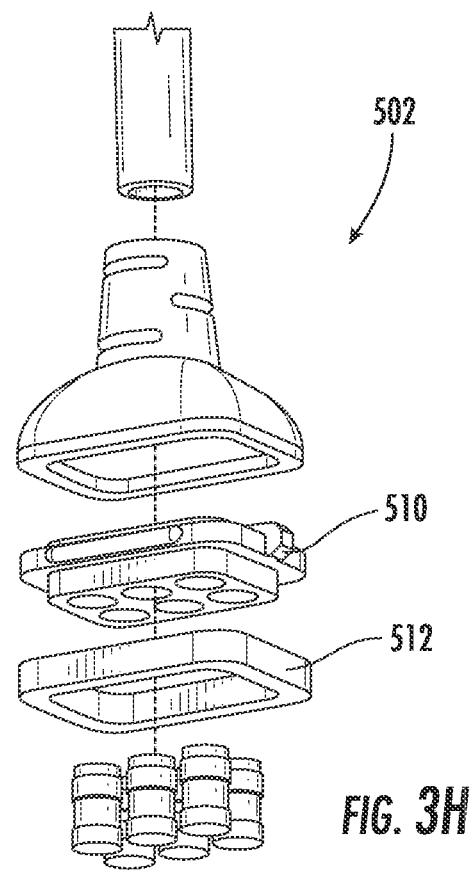
FIG. 3H illustrates an exploded, perspective view of the pogo pin connector and socket assembly of FIG. 3G.
Figure 4A:
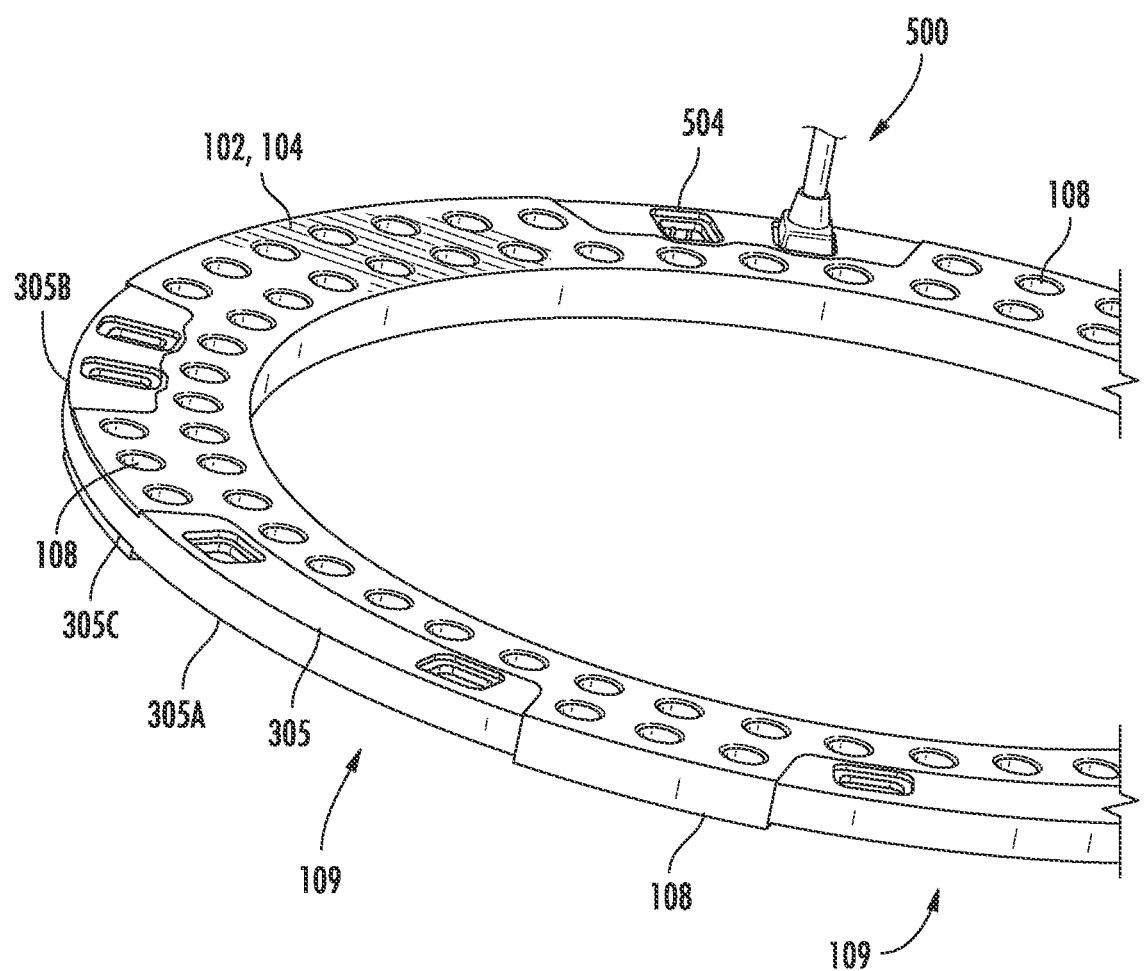
FIG. 4A illustrates a perspective view of detachable PCB modules coupled to a ring or platform of a spatial frame, the PCB modules coupled to the ring or platform via non-threaded connectors in accordance with one or more features of the present disclosure.
Figure 4B:
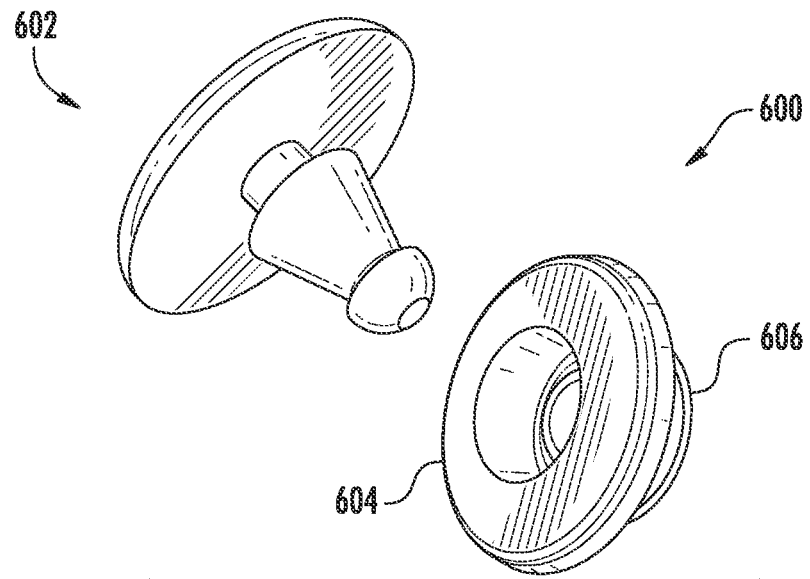
FIG. 4B illustrates a perspective view of an embodiment of the non-threaded connector used in FIG. 4A to couple the PCB module to the ring or platform.
Figure 4C:
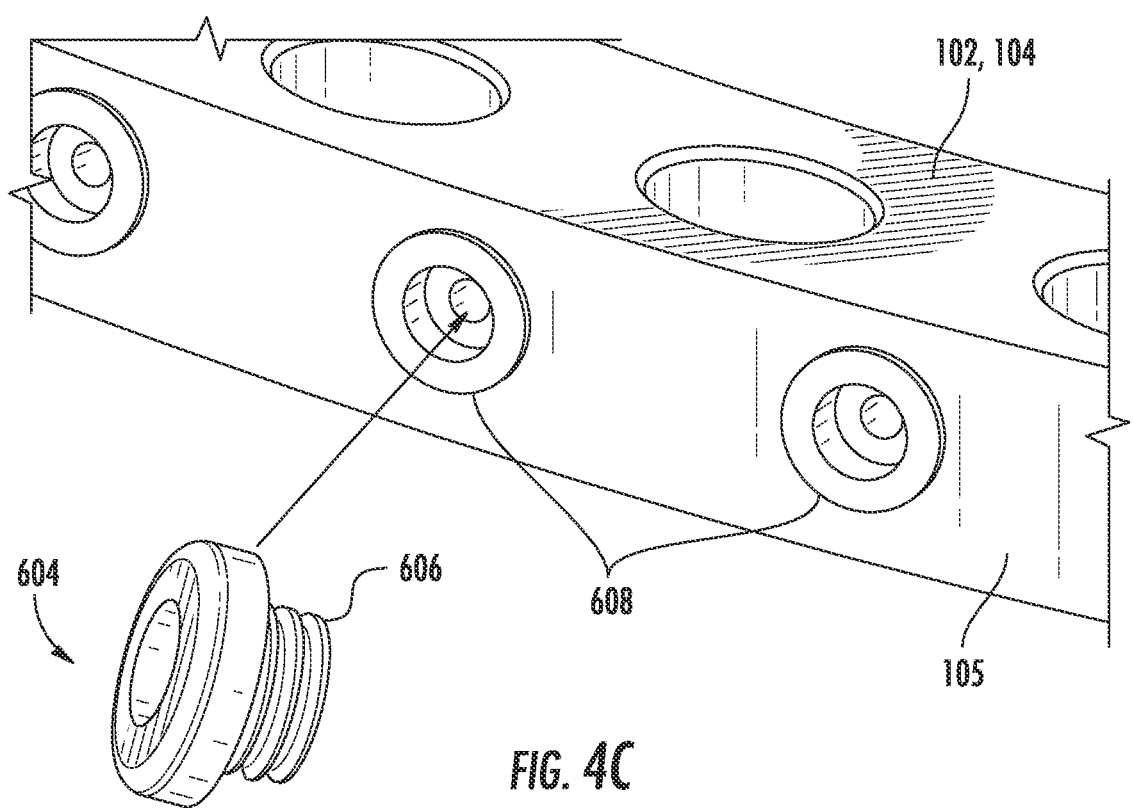
FIG. 4C illustrates a perspective view of the female connector shown in FIG. 4B being threadably coupled to the ring or platform.
Figure 6A:
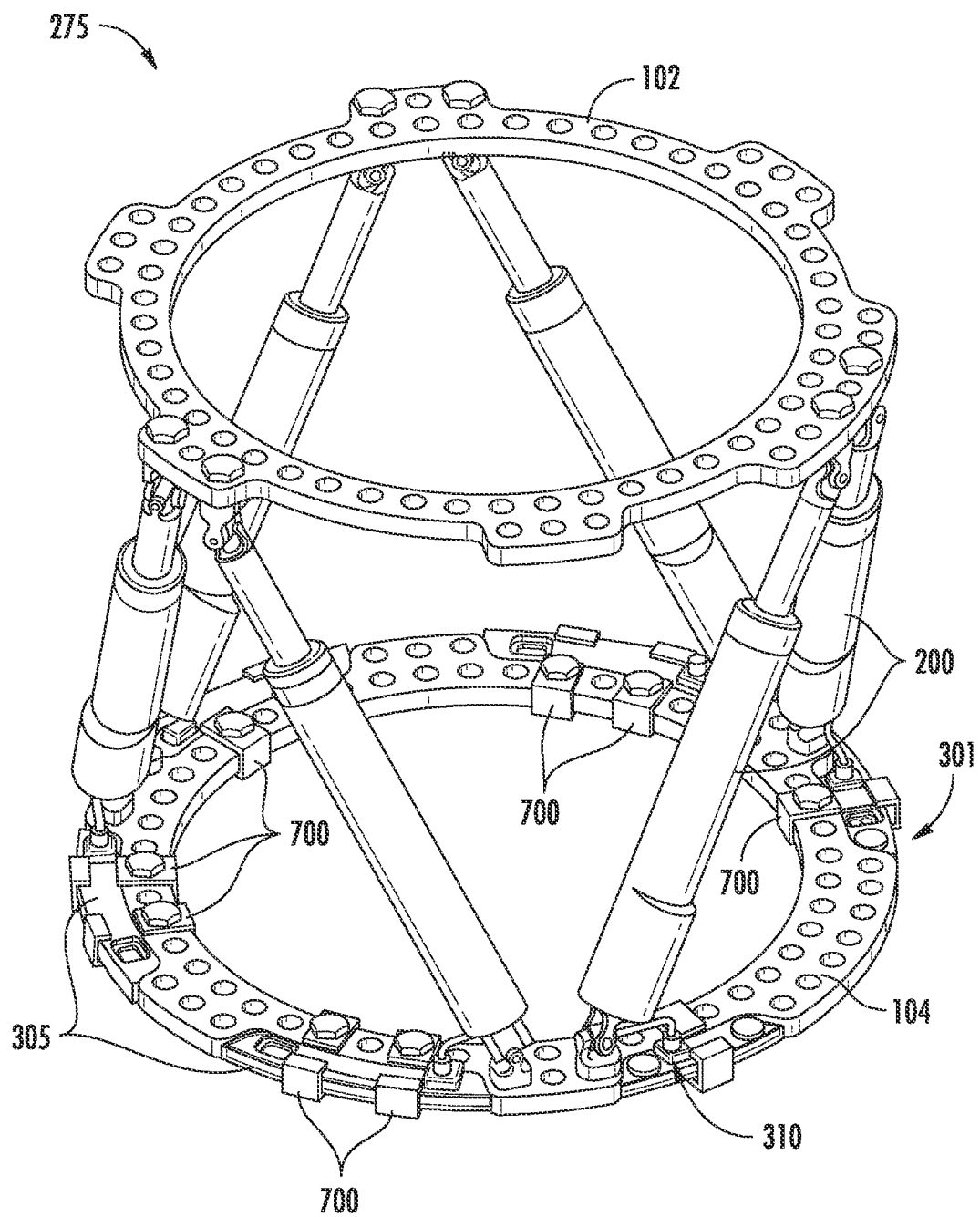
FIG. 6A illustrates a perspective view of an embodiment of an automated and/or motorized spatial frame including a Smart Ring, the Smart Ring including three-separate PCB modules coupled to a standard ring or platform utilizing a plurality of clips in accordance with one or more features of the present disclosure.
Figure 6B:
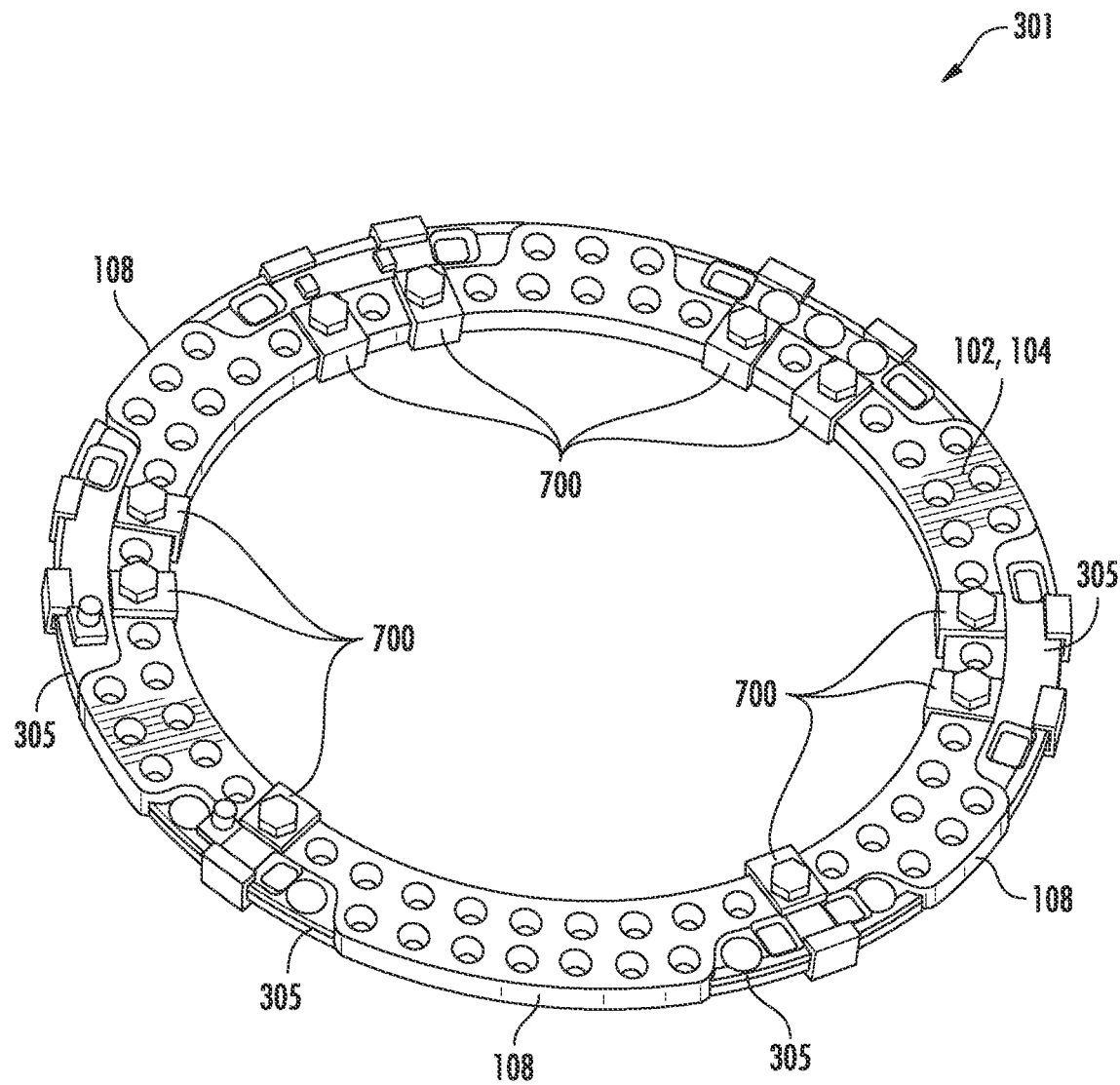
FIG. 6B illustrates a perspective view of the Smart Ring shown in FIG. 6A, the PCB modules being coupled to the ring or platform utilizing a plurality of clips.
Figure 6C:
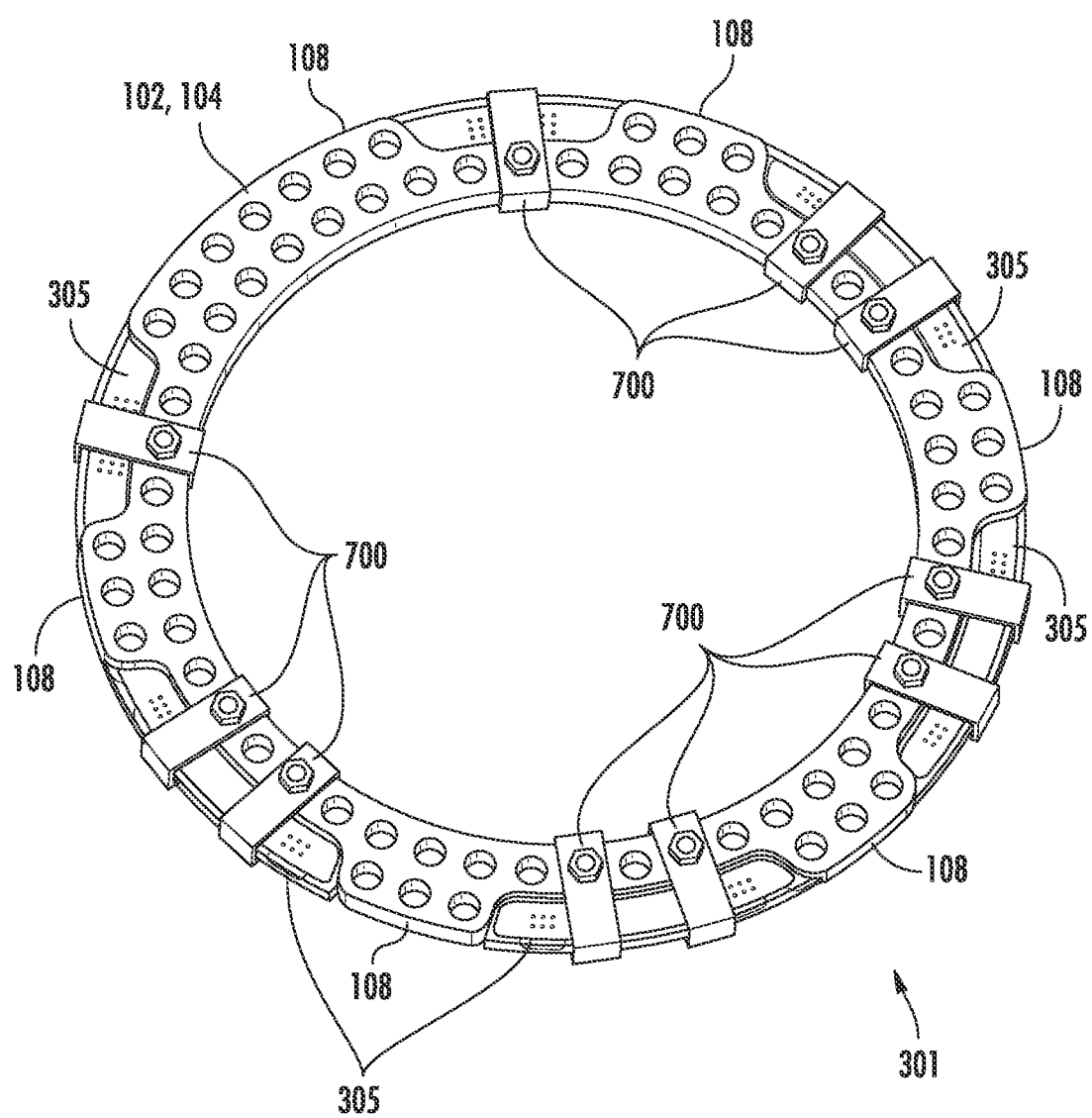
FIG. 6C illustrates a top view of the Smart Ring shown in FIG. 6A, the PCB modules being coupled to the ring or platform utilizing a plurality of clips.
Figure 6D:
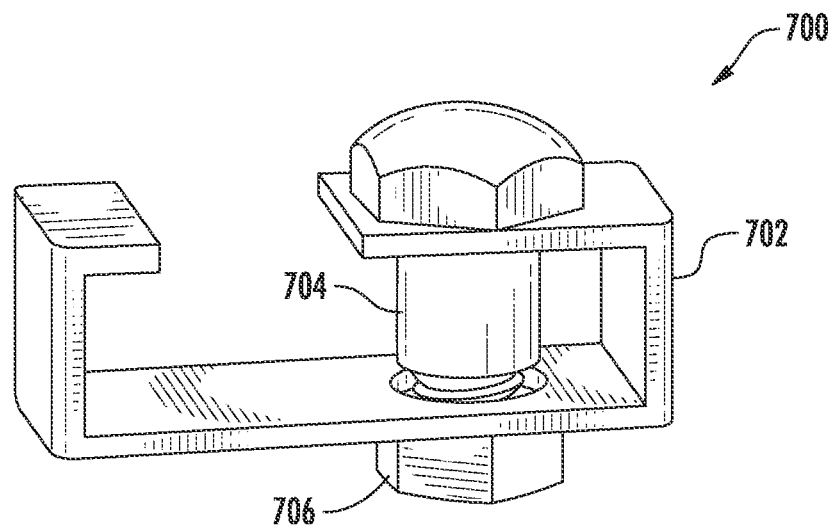
FIG. 6D illustrates a perspective view of the clips shown in FIG. 6A, the clips being used to couple the PCB modules to the ring or platform.
Figure 6E:
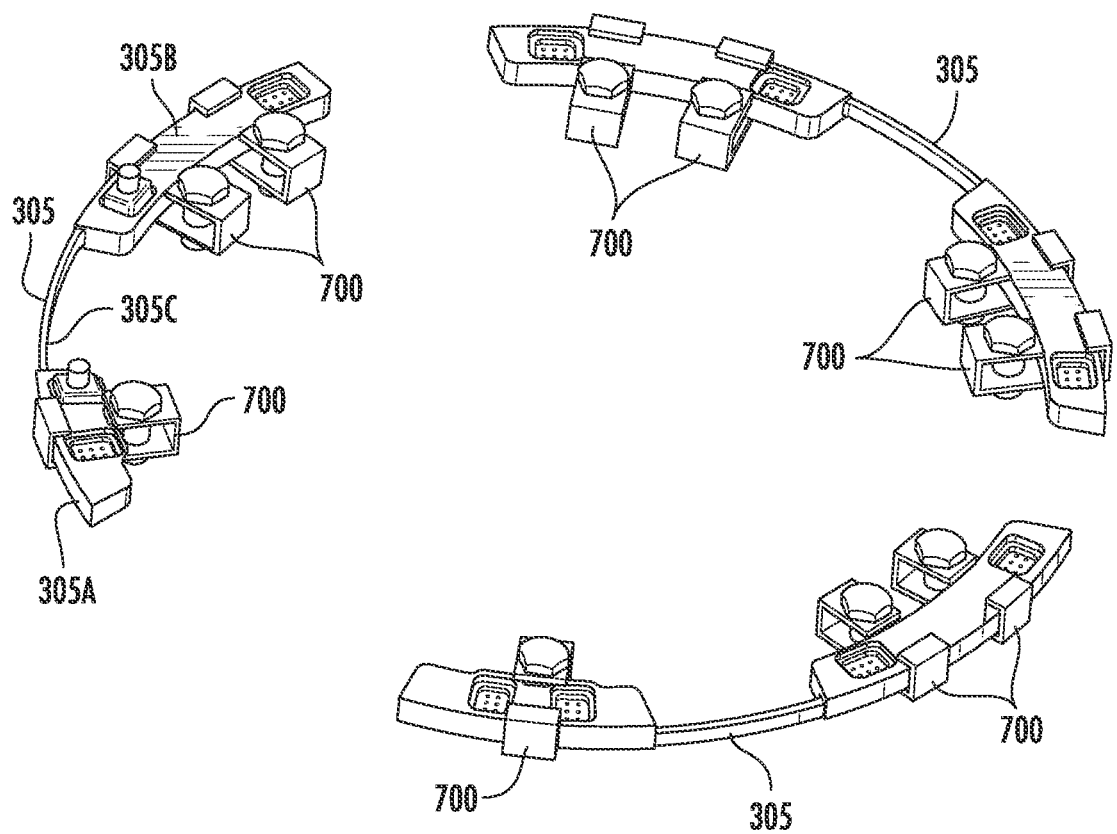
FIG. 6E illustrates a perspective view of the PCB modules and clips shown in FIG. 6A, the clips being used to couple the PCB modules to the ring or platform.

In some embodiments, the Smart Ring 301 including the PCB modules 305 may be hermetically sealed using any suitable method and/or material now known or hereafter developed such as, for example, a press-fit plastic or metal lid or a biocompatible potting compound (e.g., medical grade epoxy, silicone elastomer, polyurethane material, etc.). For example, referring to FIGS. 3E and 3F, in some embodiments, after assembly of the Smart Ring 301 (e.g., after assembly of the PCB modules 305 in the pockets or spaces 109, the pockets or spaces 109 may be overmoulded 400 to encapsulate the electronics (e.g., PCB modules 305). FIG. 3E illustrating the underlying electronics while FIG. 3F omits the underlying electronics for increased clarity.

In use, the overmoulding 400 protects the components on the PCB modules 305 from mechanical forces and environmental pollutants that can damage them over time. For example, the overmoulding 400 protects the solder joints, the traces required for electrical conductivity between the batteries and the PCB compartments, etc. from expected stresses. In addition, a potting compound could be used to create an interface between the PCB electronics and the overmoulding layer providing additional protection.

The overmoulding 400 may be any suitable overmoulding material now known or hereafter developed including, for example, EP37-3FLF two-part epoxy resin and MasterSil MS151 two-part silicone adhesive supplied by Masterbond Inc. (Hackensack, NJ, US). In use, the EP37-3FLF epoxy resin provides the benefits of a Shore D hardness of 30, good optical clarity and excellent adhesion to metal (e.g., aluminum ring). In use, the overmoulding may be coupled to the metal (e.g., aluminum ring) by any suitable method now known or hereafter developed including, for example, an adhesive, fasteners passing through the overmoulding, fasteners passing into the aluminum platform, etc.

Thus described, in some embodiments, the control unit may be arranged and configured as three separate and independent ring-shaped PCB modules 305. In use, each of the PCB modules 305 is arranged and configured to be coupled to the platform 102, 104 within the existing spaces or pockets 109 between the six laterally extending tabs 108 formed on the platforms 102, 104. Each PCB module 305 may include a battery (e.g., a plurality of coin cells), a micro-controller, and connectors (e.g., pin pogo connectors) to provide power and positional control to the respective motorized struts 200 coupled to each PCB module 305. In some embodiments, each PCB module 305 may communicate with each of the other PCB modules 305 via, for example, Low Energy Bluetooth, a wired connection, etc. Each of the PCB modules 305 may be potted or molded in a biocompatible resin such as, for example, an epoxy resin to provide IP68 water proofing that allows the patient to have showers, bath and to exercise in a therapeutic pool.

The PCB modules 305 may be coupled to the spatial frame (e.g., platform 102, 104) via any suitable mechanism now known or hereafter developed. For example, the PCB modules 305 could be permanently bonded to the platform 102, 104. However, one disadvantage with permanently bonding the PCB modules to the platforms is that the platforms need to be sterilizable and installed in a surgical environment. They also require specialized machining operations to create the optional floors (as illustrated in FIG. 3C) in the pockets 109 between the tabs 108 to accommodate the PCB modules 305.

As such, in accordance with one or more features of the present disclosure, the PCB modules 305 and platforms 102, 104 may be arranged and configured to enable the PCB modules 305 to be detachably coupled to the platforms 102, 104. In some embodiments, the PCB modules 305 are arranged and configured to be coupled to the platforms 102, 104 using one or more quick-coupling mechanical fasteners as will be disclosed herein. As will be described herein, the quick-coupling mechanical fasteners are arranged and configured as "no-turning" or non-threaded quick-coupling mechanical fasteners (e.g., the quick-coupling mechanical fasteners are configured to mate or couple without any rotation, which is contrary to many prior-art fasteners that require at least a quarter of a turn to engage and lock the mating parts).

Thus arranged, the PCB modules 305 may be coupled to the platforms 102, 104 in a more efficient and quicker manner as compared to conventional threaded fasteners such as screws. As will be described in greater detail herein, in some embodiments, the quick-coupling mechanical fasteners may be configured as interference fit connectors, snap-fit connectors, buttons, toggles, studs, islet and cap, poppers, eyelets, buckles, Velcro (e.g., Velcro hook and loop tape, which can hold 1 lbs per square inch up to 5 lbs), adhesive tape, etc. In some embodiments, the quick-coupling mechanical fasteners may be configured as a flexible magnet strip. In use, the magnetic strip may be magnetic on a first side and an adhesive on the reverse side. In some embodiments, the magnetic side may be magnetized to itself rendering it ideal for mating to plastic parts. In various embodiments, the magnet strip may be configured with a strength rating of 10 pounds of pull per linear foot.

With reference to FIGS. 4A-4D, in some embodiments, the PCB modules 305 are designed to fit within the spaces or pockets 109 between existing tabs 108 formed on the platforms 102, 104. The three detachable control or PCB modules 305 can be coupled to the platforms 102, 104 using interconnecting male and female connectors 600 to connect the PCB modules 305 to the rings or platforms 102, 104. In use, the interconnecting male and female connectors 600 are arranged and configured to mate, couple, engage, etc. with each other via an interference fit connection. That is, in use, the male connector is configured to be inserted into the female connector by forcing one of the parts to elastically deform. For example, the male connector may be arranged and configured with a diameter that is slightly smaller than the corresponding opening formed in the female connector. Alternatively, the interconnecting male and female connectors 600 may be arranged and configured to mate, couple, engage, etc. with each other via a snap-fit connection or a ratchet type connection. In use, the interconnecting male and female connectors 600 may be snap-fitted or ratcheted together.

In some embodiments, the female connectors 604 may be positioned, installed, integrated with the platforms 102, 104. For example, with reference to FIGS. 4B-4D, the male connector 602 may be coupled, integrated, etc. with the individual PCBs modules 305 and the female connector 604 may be coupled, integrated, etc. with the platform 102, 104, or vice-versa. For example, in some embodiments, the female connectors 604 may be positioned in a side wall 105 of the platforms 102, 104, between the laterally extending tabs 108. As illustrated, in some embodiments, the female connectors 604 may include external threads 606 that may be threaded into an internally threaded hole 608 formed in the sidewalls 105 of the platforms 102, 104. The male connector 602 may be molded into the PCB modules 305. In use, the male connector 602 coupled to the PCB modules 305 may be inserted into the female connector 604 thereby coupling the PCB modules 305 to the platforms 102, 104. In some embodiments, e.g., 180 mm diameter full ringed platform, there may be twenty pairs of connectors 600 located between the tabs 108 of a platform 102, 104. Thus arranged, the PCB modules 305 may be quickly and efficiently coupled to the platforms 102, 104 using a non-threaded connection.

Alternatively, the control unit 300 or PCB modules 305 may be coupled to the platforms 102, 104 using other suitable non-threaded connectors such as, for example, buttons, toggles, studs, islet and cap, poppers, eyelets, buckles, Velcro, adhesive tape, magnetic tape or strips, etc. For example, referring to FIG. 5, an interconnecting islet and cap assembly 650 is illustrated. In use, similar to the interconnecting male and female connectors, the islet and cap assembly 650 includes a male islet 652 and a female cap 654, which may be used in place of the interconnecting male and female connectors 600 to non-threadably couple the PCB modules 305 to the platform or ring 102, 104.

Referring to FIGS. 6A-6E, in yet another embodiment, the PCB modules 305 may be coupled to the rings or platforms 102, 104 using a plurality of clips or clip assemblies 700. As illustrated, in some embodiments, the clips 700 includes a bracket 702 and a shoulder bolt 704 and a nut assembly 706, although other suitable mechanisms or assemblies for coupling the bracket 702 to the platforms 102, 104 may be used. The bracket 702 is arranged and configured to surround the PCB module 305 and the platform 102, 104 to couple the PCB modules 305 to the platform 102, 104. In use, the clips 700 can be positioned about the PCB modules 305 and platform 102, 104 as needed. Once positioned, the shoulder bolt 704 may be passed through the bracket 702 and through an existing shoulder bolt opening currently provided in the platforms 102, 104. Thus arranged, the clips 700 enable the medical provider to position the clips 700 circumferentially about the platform 102, 104 without limitation. In addition, the clips 700 enable usage of existing platforms without any modification.

In some embodiments, the clips may be approximately 12 mm wide×30 mm long×1 mm thick and may be manufactured from either a polymeric material such as nylon or a metal such as aluminum.

Once the PCB modules 305 are coupled to the platform 102, 104, the motorized struts 200 may be connected to the pogo pin connectors located on the Smart Ring.

In accordance with one or more features of the present disclosure, by providing a detachable coupling mechanism between the PCB modules and the platform, the advantage of providing semi-continuous actuation without compromising the ability to carry out complex limb deformity corrections with a spatial frame is achieved. The PCB modules can be attached to the frame in a clinic setting negating the need for any sterilization. It also simplifies the overall design of the automated and/or motorized spatial frame reducing the risk of an electrical failure during application.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Any embodiment or feature of any section, portion, or any other component shown or particularly described in relation to various embodiments of similar sections, portions, or components herein may be interchangeably applied to any other similar embodiment or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

We claim:

1. A motorized spatial frame comprising:
   a first platform including a plurality of circumferential tabs and spaces;
   a second platform;
   a plurality of motorized struts coupled to the first and second platforms, each of the plurality of motorized struts configured to extend and retract in response to one or more electrical signals; and
   one or more print circuit board (PCB) modules, each of the one or more PCB modules is configured to be selectively coupled to the first platform so that each of the one or more PCB modules is positioned at least partially within the spaces between the tabs formed on the first platform such that each PCB module resides within a height as defined by top and bottom surfaces of the first platform, each of the one or more PCB modules including:
   a control unit electrically connected to one or more of the plurality of the motorized struts, the control unit configured to provide the one or more electrical signals to the plurality of motorized struts;
   a power source configured to supply power to the plurality of motorized struts; and
   a plurality of non-threaded connector assemblies arranged and configured to detachably couple each of the one or more PCB modules to the first platform;

wherein each of the one or more PCB modules includes a control unit module and a power supply module arranged and configured to provide the one or more electrical signals and to supply power to one or more of the plurality of motorized struts.

2. The motorized spatial frame of claim 1, wherein each of the one or more PCB modules is arranged and configured to exchange data with one or more of the plurality of motorized struts to which it is connected, the data including length adjustment instructions and timing instructions.

3. A motorized spatial frame of claim 1, comprising:
a first platform including a plurality of circumferential tabs and spaces;
a second platform;
a plurality of motorized struts coupled to the first and second platforms, each of the plurality of motorized struts configured to extend and retract in response to one or more electrical signals; and
one or more print circuit board (PCB) modules, each of the one or more PCB modules is configured to be selectively coupled to the first platform so that each of the one or more PCB modules is positioned at least partially within the spaces between the tabs formed on the first platform such that each PCB module resides within a height as defined by top and bottom surfaces of the first platform, each of the one or more PCB modules including:
  a control unit electrically connected to one or more of the plurality of the motorized struts, the control unit configured to provide the one or more electrical signals to the plurality of motorized struts;
  a power source configured to supply power to the plurality of motorized struts; and
  a plurality of non-threaded connector assemblies arranged and configured to detachably couple each of the one or more PCB modules to the first platform;
wherein the first platform includes a plurality of control units, a plurality of power supplies, and first, second, and third separate and independent PCB modules, each of the PCB modules including a power supply module including one of the plurality of power supplies and a control unit module including one of the plurality of control units, each of the power supply modules and each of the control unit modules being arranged and configured to reside within spaces formed between tabs on the first platform.

4. The motorized spatial frame of claim 1, wherein the plurality of non-threaded connector assemblies include non-threaded interconnecting male and female connectors.

5. The motorized spatial frame of claim 4, wherein the female connectors are integrated into the first platform and the male connectors are integrated into the one or more PCB modules.

6. The motorized spatial frame of claim 5, wherein the female connectors include external threads for threadably engaging an internally threaded hole formed in a sidewall of the first platform.

7. The motorized spatial frame of claim 6, wherein the male connectors are molded with the one or more PCB modules.

8. The motorized spatial frame of claim 4, wherein the plurality of non-threaded connector assemblies are configured as non-threaded connectors selected from one of buttons, toggles, studs, islet and cap, poppers, eyelets, and magnetic strips.

9. A motorized spatial frame comprising:
a first platform including a plurality of circumferential tabs and spaces;
a second platform;
a plurality of motorized struts coupled to the first and second platforms, each of the plurality of motorized struts configured to extend and retract in response to one or more electrical signals; and
one or more print circuit board (PCB) modules, each of the one or more PCB modules is configured to be selectively coupled to the first platform so that each of the one or more PCB modules is positioned at least partially within the spaces between the tabs formed on the first platform such that each PCB module resides within a height as defined by top and bottom surfaces of the first platform, each of the one or more PCB modules including:
  a control unit electrically connected to one or more of the plurality of the motorized struts, the control unit configured to provide the one or more electrical signals to the plurality of motorized struts;
  a power source configured to supply power to the plurality of motorized struts; and
  a plurality of clips arranged and configured to detachably couple each of the PCB modules to the first platform;
wherein each of the one or more PCB modules is arranged and configured to provide the one or more electrical signals and to supply power to one or more of the plurality of motorized struts.

10. The motorized spatial frame of claim 9, wherein each of the one or more PCB modules is arranged and configured to exchange data with one or more of the plurality of motorized struts to which it is connected, the data including length adjustment instructions and timing instructions.

11. The motorized spatial frame of claim 9, wherein the plurality of clips include a bracket and a shoulder bolt and nut assembly.

12. The motorized spatial frame of claim 11, wherein the bracket is arranged and configured to surround the one or more PCB modules and the first platform to couple the one or more PCB modules to the first platform.

13. The motorized spatial frame of claim 12, wherein the shoulder bolt passes through the bracket and through an existing shoulder bolt opening formed in the first platform.

14. A motorized spatial frame comprising:
a first platform including a plurality of circumferential tabs and spaces;
a second platform;
a plurality of motorized struts coupled to the first and second platforms, each of the plurality of motorized struts configured to extend and retract in response to one or more electrical signals; and
one or more print circuit board (PCB) modules, each of the one or more PCB modules is configured to be selectively coupled to the first platform so that each of the one or more PCB modules is positioned at least partially within the spaces between the tabs formed on the first platform such that each PCB module resides within a height as defined by top and bottom surfaces of the first platform, each of the one or more PCB modules including:
  a control unit electrically connected to one or more of the plurality of the motorized struts, the control unit configured to provide the one or more electrical signals to the plurality of motorized struts;
  a power source configured to supply power to the plurality of motorized struts; and a plurality of non-threaded connector assemblies arranged and configured to detachably couple each of the one or more PCB modules to the first platform, the plurality of non-threaded connector assemblies including non-threaded interconnecting male connectors integrated into the one or more PCB modules and female connectors integrated into the first platform, the female connectors including external threads for threadably engaging an internally threaded hole formed in a sidewall of the first platform.

15. The motorized spatial frame of claim 14, wherein each of the one or more PCB modules includes a control unit module and a power supply module arranged and configured to provide the one or more electrical signals and to supply power to one or more of the plurality of motorized struts.

16. The motorized spatial frame of claim 15, wherein each of the one or more PCB modules is arranged and configured to exchange data with one or more of the plurality of motorized struts to which it is connected, the data including length adjustment instructions and timing instructions.

17. The motorized spatial frame of claim 14, wherein the first platform includes a plurality of control units, a plurality of power supplies, and first, second, and third separate and independent PCB modules, each of the PCB modules including a power supply module including one of the plurality of power supplies and a control unit module including one of the plurality of control units, each of the power supply modules and each of the control unit modules being arranged and configured to reside within spaces formed between tabs on the first platform.

18. The motorized spatial frame of claim 14, wherein the male connectors are molded with the one or more PCB modules.

* * * * *